US007625760B2

(12) United States Patent
Kitaguchi et al.

(10) Patent No.: US 7,625,760 B2
(45) Date of Patent: Dec. 1, 2009

(54) ANALYZING CARTRIDGE AND LIQUID FEED CONTROL DEVICE

(75) Inventors: Nobuya Kitaguchi, Fuji (JP); Akira Kiguchi, Yokohama (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 743 days.

(21) Appl. No.: 11/056,247

(22) Filed: Feb. 14, 2005

(65) Prior Publication Data
US 2005/0148091 A1    Jul. 7, 2005

Related U.S. Application Data

(62) Division of application No. 10/049,239, filed as application No. PCT/JP00/05416 on Aug. 11, 2000, now abandoned.

(30) Foreign Application Priority Data
Nov. 8, 1999  (JP)  .................................. 11-227624

(51) Int. Cl.
*G01N 21/00* (2006.01)
*G01N 30/02* (2006.01)
*G01N 1/10* (2006.01)
*G01N 21/03* (2006.01)

(52) U.S. Cl. .......................... 436/165; 436/180; 422/57; 422/58; 422/70

(58) Field of Classification Search .................... 422/57, 422/58, 70; 436/165, 180
See application file for complete search history.

(56) References Cited

U.S. PATENT DOCUMENTS 3,785,771 A * 1/1974 Luchsinger et al. ......... 436/164

(Continued)

FOREIGN PATENT DOCUMENTS

EP           0 212 314         3/1987

(Continued)

OTHER PUBLICATIONS

Izumi Kanai, "An Outline of Clinical Laboratory Test," Kanahara Publishing Company, 1998.

(Continued)

*Primary Examiner*—Jill Warden
*Assistant Examiner*—Lore Jarrett
(74) *Attorney, Agent, or Firm*—Finnegan, Henderson, Farabow, Garrett & Dunner, L.L.P.

(57) ABSTRACT

An analyzing cartridge and method for using it to analyze a sample having a plurality of reservoirs and capillaries connected for communication between these reservoirs and is provided therein with a reagent required for analysis. The reservoirs are provided with openings leading to the outside of the cartridge, and the openings are covered with vents each consisting of a gas-permeable/non-liquid-permeable, hydrophobic, porous membrane. The analyzing cartridge requires only trace amounts of a sample and a reagent and no maintenance. It is provided with a non-fluid reagent in vent-carrying reservoirs thereby making it possible to formulate a very trace amount of reagent solution in the cartridge by injecting a reagent dissolving liquid into the reservoirs immediately before analyzing. A liquid feed control device controls the feeding of the liquid between the reservoirs via the capillaries when it is attached to the cartridge to allow or control the entry/exit of air via the vents.

13 Claims, 11 Drawing Sheets

U.S. PATENT DOCUMENTS

| | | | |
|---|---|---|---|
| 4,439,492 | A | 3/1984 | Wada et al. |
| 4,756,884 | A | 7/1988 | Hillman |
| 4,965,047 | A * | 10/1990 | Hammond .................. 422/58 |
| 5,147,607 | A | 9/1992 | Michida |
| 5,149,501 | A * | 9/1992 | Babson et al. ............... 422/58 |
| 5,212,065 | A | 5/1993 | Pegg et al. |
| 5,223,219 | A | 6/1993 | Subramanian et al. |
| 5,229,297 | A * | 7/1993 | Schnipelsky et al. .......... 436/94 |
| 5,230,866 | A | 7/1993 | Shartle et al. |
| 5,272,093 | A * | 12/1993 | Silva et al. .................. 436/180 |
| 5,290,518 | A * | 3/1994 | Johnson ...................... 422/58 |
| 5,478,751 | A | 12/1995 | Oosta et al. |
| 5,856,174 | A | 1/1999 | Lipshutz |
| 5,858,195 | A | 1/1999 | Ramsey |
| 5,904,424 | A | 5/1999 | Schwesinger et al. |
| 6,197,595 | B1 | 3/2001 | Anderson et al. |
| 6,468,732 | B1 * | 10/2002 | Malin et al. .................... 435/2 |
| 7,122,153 | B2 * | 10/2006 | Ho .............................. 422/58 |
| 7,473,397 | B2 * | 1/2009 | Griffin et al. ................. 422/57 |

FOREIGN PATENT DOCUMENTS

| | | |
|---|---|---|
| JP | 57-17659 | 1/1982 |
| JP | 57008131 | 1/1982 |
| JP | 33144 | 9/1984 |
| JP | 60174933 | 9/1985 |
| JP | 02002812 | 1/1990 |
| JP | 2-87067 | 3/1990 |
| JP | 2-88970 | 3/1990 |
| JP | 2-293640 | 4/1990 |
| JP | 2-245655 | 10/1990 |
| JP | 3-226666 | 10/1991 |
| JP | 03223674 | 10/1991 |
| JP | 4-53384 | 8/1992 |
| JP | 04369467 | 12/1992 |
| JP | 06283830 | 10/1994 |
| JP | 8-62225 | 3/1996 |
| JP | 08114539 | 5/1996 |
| JP | 08160031 | 6/1996 |
| JP | 08233778 | 9/1996 |
| JP | 9-500809 | 1/1997 |
| JP | 09-504732 | 5/1997 |
| JP | 09138195 | 5/1997 |
| JP | 09229883 | 5/1997 |
| JP | 09196739 | 7/1997 |
| JP | 09196920 | 7/1997 |
| JP | 10-501340 | 2/1998 |
| JP | 1014277 | 5/1998 |
| JP | 10128783 | 5/1998 |
| JP | 10181586 | 7/1998 |
| JP | 11245255 | 9/1999 |
| JP | 11245270 | 9/1999 |
| JP | 2000002675 | 1/2000 |
| JP | 2000002677 | 1/2000 |
| JP | 2001165939 | 6/2001 |
| WO | WO 93/04195 | 3/1993 |
| WO | WO 93/25889 | 12/1993 |
| WO | WO 97/02357 | 1/1997 |
| WO | WO 99/52633 | 10/1999 |
| WO | WO 99/64846 | 12/1999 |

OTHER PUBLICATIONS

Randy M. McCormick et al., "Microchannel Electrophoretic Separations of DNA in Injection-Molded Plastic Substrates," *Anal. Chem.*, 1997, pp. 2626-2630.

Teruo Fujii et al., "Micro Chemical Analysis System Fabricated by Silicone Elastomer Molding Processes," Document of Electricity Academy Workshop: Society for Study of Chemical Sensor System CS-99-1 to 12, pp. 19-22, Mar. 16, 1999.

Rolfe C. Anderson et al., "Microfluidic Biochemical Analysis System," 1997 International Conference on Solid-State Sensors and Actuators, Chicago, Jun. 16-19, 1997.

"Improvement of Flow Length of Injection Molded Polymer Products Utilizing a Radiative Heating," Molding Symposia '95, pp. 241-242 (1995).

Molding '96, pp. 69-72 (1996).

*Synthetic Resin*, vol. 42(1), pp. 48-52 (1992).

A.C. Boccara et al., Thermo-optical spectroscopy: Detection by the "mirage effect," *App. Phys. Lett.* 36(2), pp. 130-132, (1980).

Colin W. Earle et al., "Simultaneous Two-Color Thermo-Optical Absorbance Detector for CapillaryZone Electrophoresis," *Journal of Liquid Chromatography*, 12(13), pp. 2575-2585 (1989).

*Analysis* No. 4, 280-284, (1997).

Masaaki Harada et al., "Photothermal Microscopy with Excitation and Probe Beams Coaxial under the Microscope and Its Application to Microparticle Analysis," *Anal. Chem.* vol. 65, pp. 2938-2940, (1993).

Kawanishi et al., *Japan Analytical Chemistry Society* vol. 44 Annual Conference Abstract, p. 119, (1995).

Shuuichi Shouji et al., "Micro Kagaku Bunseki System," Transactions, the Institute of Electronics, Information and Communication Engineers, (Japan), 1998, vol. J81-C-I, No. 7, pp. 385-393.

Kazuo Hosokawa et al., "Hydrophobic Microcapillary Vent for Pneumatic Manipulation of Liquid in μTaz," Kluwer Academic Publishers, 1998, pp. 307-310.

Hiroaki Nakanishi et al., "Micro-fabrication and analytical performances of quartz and glass microchips for electrophoresis,"*Bunseki Kagaku*, vol. 47, No. 6, pp. 361-368 (1998), *The Japan Society for Analytical Chemistry*.

Aoyama, N. Clinical Examination, 41: 1014-1019 (1997).

* cited by examiner

FIG. 3
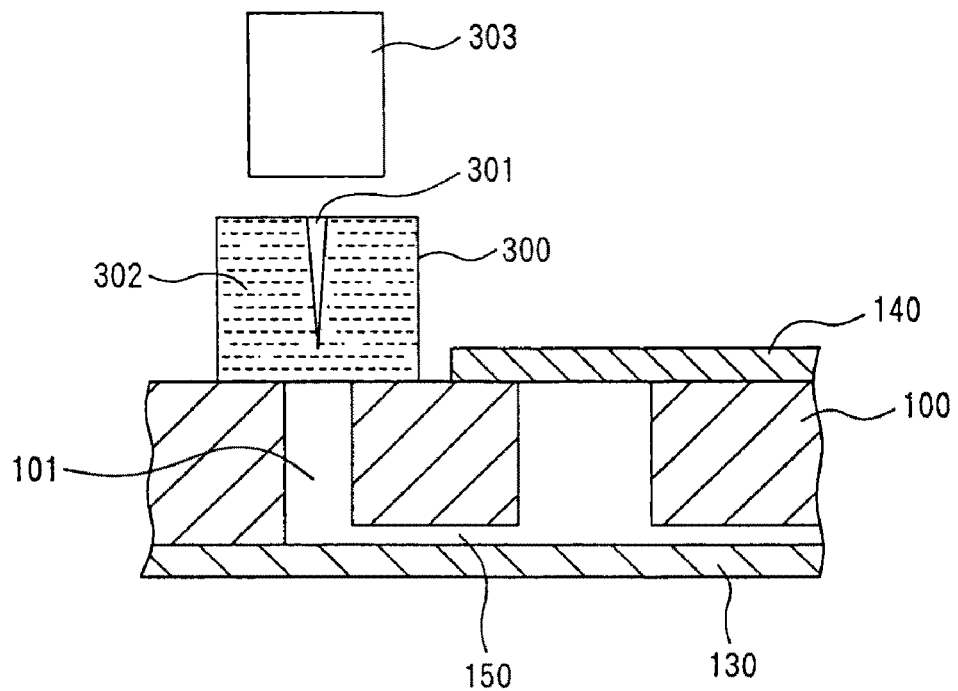
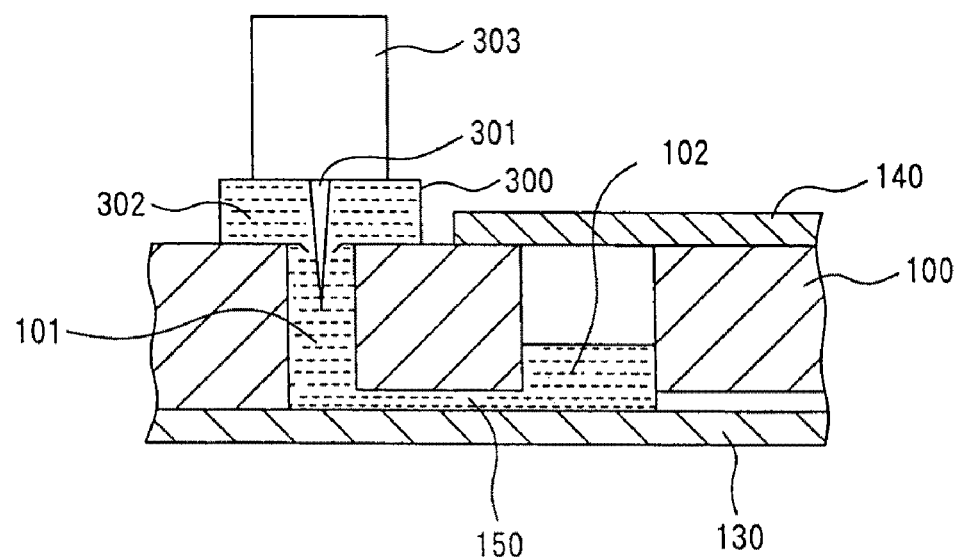

FIG. 10
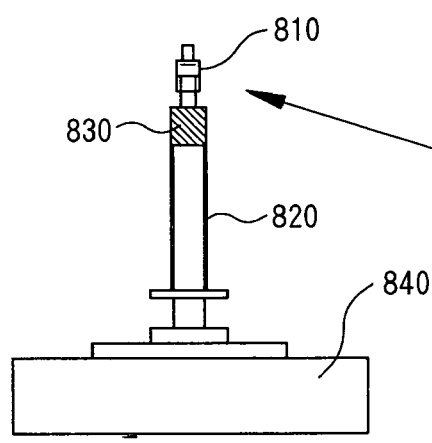
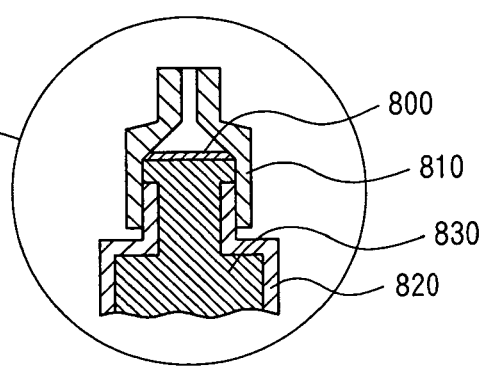
FIG. 11
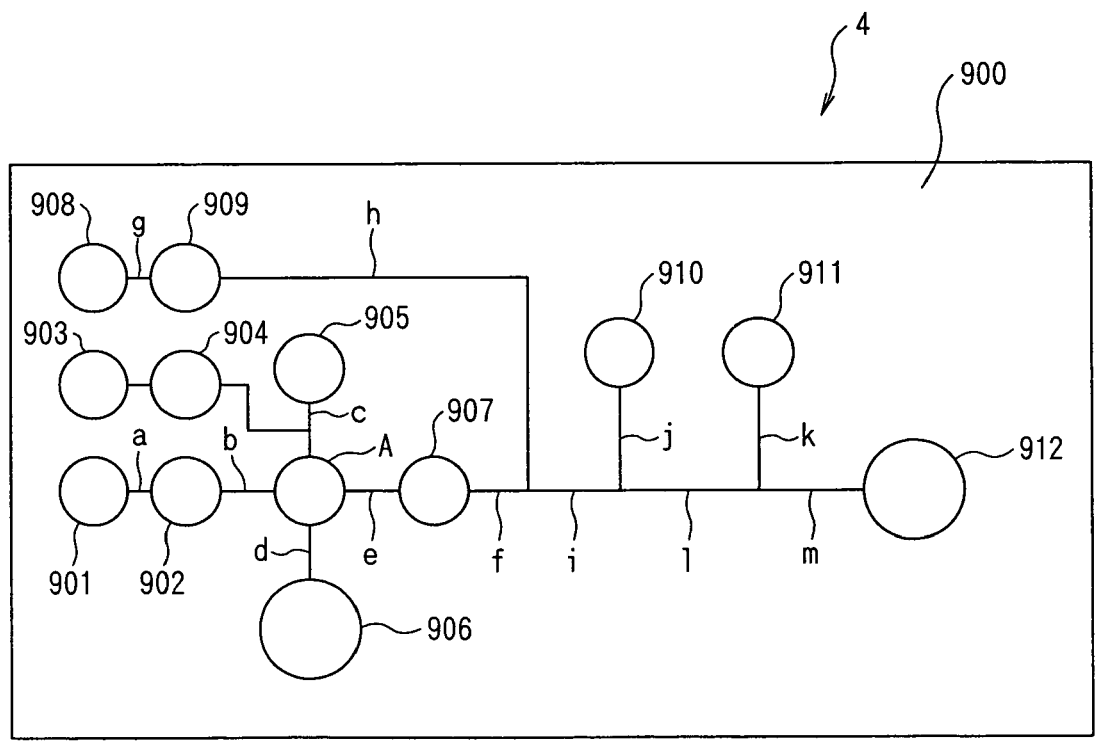

ANALYZING CARTRIDGE AND LIQUID FEED CONTROL DEVICE

This application is a Divisional of U.S. application Ser. No. 10/049,239 filed Feb. 11, 2002, now abandoned, which is a §371 of International Application No. PCT/JP00/05416 filed Aug. 11, 2000 and claims priority of Japanese Application No. 11-227,624, filed Nov. 8, 1999.

TECHNICAL FIELD

The present invention relates to an analyzing cartridge for use in analysis of a trace amount of sample, enabling analysis and detection to be carried out conveniently, and a method for producing the same. The invention also relates to an analysis method using the analyzing cartridge. In addition, the invention relates to a liquid feed control device that is attached to the analyzing cartridge, and controls the feeding of liquid in the analyzing cartridge.

BACKGROUND ART

Attention is being given to the importance of analyses and measurements carried out at or near the site where the analyses and measurements are required (hereinafter referred to as "POC (point of care) analyses and the like" collectively), such as analyses for bedside diagnosis (POC analyses) in which a measurement required for medical diagnosis is carried out near a patient, analyses of hazardous substances in rivers and wastes carried out at sites such as rivers and wastes treatment plants, and contamination tests at individual sites for cooking, harvest and importation of foods. And, in recent years, development of measurement methods and apparatuses suitable for these POC analyses and the like has been considered as an important matter.

In these POC analyses and the like, it is required that analysis be able to be carried out conveniently, for a short time and inexpensively, and particularly in analyses for medical diagnosis, reduction in analysis time and reduction in the amount of sample required for analysis to a very low level are important challenges to be addressed.

In the blood test, for example, if the amount of sample required for analysis is very small, the amount of blood to be collected can be reduced, thus alleviating burdens on patients, and increasing the possibility of application to at-home medical care such as self analysis by self blood-collection. Also, if the amount of sample required for analysis is very small, then the amount of reagent for use in analysis can also be reduced to a very low level, thus making it possible to reduce costs involved in the analysis. In addition, studies are continued for reduction in the amount of sample to a very low level and reduction in analysis time, because the goal of reducing the amount of wastes can be thereby achieved at the same time.

In the case of qualitative analysis in which a determination is made by visual observation or the like, methods in which a sample such as blood, urine and polluted water is directly contacted with a test paper impregnated with an analyzing reagent are widely used. However, in the case of quantitative analysis of blood biochemistry in which the enzyme activity in the blood and the amount of substance to be measured are analyzed, quantifiability is required, and therefore most of the methods currently used in medical practice are such that an reagent solution, buffer and the like set in an analyzer are mixed and quantitatively reacted with a sample weighed and taken in a cuvette or test tube in the analyzer using an automatic pipetter or the like to make a detection with a detection device.

However, in the case of these methods, the reagent solution, buffer and the like set in the analyzer should be replenished as appropriate. Also, there are possibilities that troubles occur such as spilling of liquid, clogging of the nozzle of the automatic pipetter and contamination due to insufficient cleaning, and analysis operators, particularly doctors and nurses in the case of POC analyses in the medical field, may significantly be burdened.

For solving the above problems, a measuring system of all-in-one-type is desired in which a required reagent solution and buffer and the like are provided in the analyzing cartridge. As one example, a method in which an internal bag containing therein the reagent and the like is encapsulated in a bag containing therein the sample, and the above described internal bag is pressed by hand to break the same, thereby mixing and reacting together the sample and the reagent and the like, and then a qualitative determination is made by visual observation is disclosed in Japanese Patent Laid-Open No. 8-160031. However, such a method is not suitable for quantitative analysis in a field of blood biochemistry and the like requiring a high level of accuracy.

Ideas of containing required reagents in the cartridge in advance are also disclosed in the apparatus structures in Japanese Patent Laid-Open No. 2-87067 and Japanese Patent Laid-Open No. 2-88970. In this case, the reagent solution and the like are contained in a small bag, and the bag is broken, whereby the reagent solution and the like are leaked into the cartridge. Also, for the method for feeding a liquid, a method using centrifugal force is adopted.

In the case where the amount of sample is large, and the amount of the reagent solution and the like for analysis is also large ranging from a few hundred μl to a few ml, the solution and the like can be encapsulated in the above described bag easily and inexpensively, and the above described method can be used without any problems. However, when the amount of sample is as small as a few μl or so, a small amount of reagent solution and the like consistent with the small amount of sample should be encapsulated in a small bag, and the bag should be broken to leak the contents, and such operations are extremely difficult with the above described method.

In addition, a technique in which a liquid reagent and the like are encapsulated in a small container provided in the cartridge, and the breakable portion (breakable seal) of the small container is broken with a pointed object or the like to let the liquid reagent leak through, and mix and quantitatively react with the blood sample is also disclosed. For example, in the cartridge for measurement of hemoglobin Alc (HbAlc) of Japanese Patent No. 2790359 (Boehringer Mannheim K.K.), gravity and capillarity force are used for feeding of liquids, the breakable seal is broken to let the liquid reagent encapsulated in the cartridge leak through into a dilution vessel having a predetermined volume, where the liquid reagent is mixed quantitatively with a sample in the capillary having a predetermined volume to carry out a measurement of hemoglobin (Hb) after hemolysis and a subsequent measurement of HbAlc with latex beads.

Also, in the cartridge for an automatic analyzer disclosed in International Patent Publication WO 93/25889, a solid reagent is encapsulated in the cartridge, and a diluent and a liquid reagent are supplied from the outside of the cartridge. And, the breakable seal is broken by a pointed object such as a nail, whereby the solid reagent is mixed with the diluent and dissolved therein, and is mixed with the blood sample together with the liquid reagent.

In addition, a cartridge having a structure in which a liquid reagent is pushed out by air through a "bursting channel" at the exit of the chamber with the liquid reagent encapsulated therein, and an air bubble generated at this time is trapped in a chamber (the bubble is not pushed out from the chip) is disclosed in International Patent Publication WO 99/52633 (Lumenal Technology Co., Ltd.).

For a method using a breakable seal like this, as in the case of the aforesaid method using a bag, if the amount of the encapsulated liquid sample is large ranging from a few hundred μl to a few ml, the liquid sample can be encapsulated easily and less expensively, but if the amount of the sample is as small as a few μl or so, the liquid sample becomes very small accordingly so that it will be extremely difficult to incorporate the breakable seal in the aforesaid small container, to inject and encapsulate a very small amount of liquid sample, to break the breakable seal, to take out the liquid sample and so on.

Also, techniques in which the liquid reagent (reagent solution) and the buffer and the like are encapsulated in the cartridge, and the liquid is fed to mix and react the same together using a centrifugal force also include techniques in Japanese Patent Publication No. 4-53384B and Japanese Patent Laid-Open No. 8-62225A.

In the methods as described above, because the reagent and the buffer are encapsulated in the cartridge in liquid states, and a mechanism to take out the liquid such as a mechanism to break the seal is required, the cartridge needs to have a very complicated structure. Also, for encapsulating the reagent in a liquid state and taking out the reagent into the reaction channel, a reagent of a few ten to a few hundred μl or more is required, and thus the cost for the reagent is increased.

In addition, in most of the above described methods, centrifugal force is used for feeding the liquid. In this method, the direction in which the liquid is fed is limited to one direction extending outwardly from the center of rotation, and rotation should be started/stopped accurately in the on/off of the feeding of liquids and so on, resulting in complicated designs for the feeding of liquids and channels. In addition, there is also a disadvantage that the analyzer with which the cartridge is equipped to carry out measurements is complicated in structure and expensive. Also, in any case, since the thickness of the capillary is in the order of millimeters, and thus a lager amount of sample is required, and the amount of reagent is increased in association therewith, the cost involved in analysis is no longer reduced, along with the aforesaid increase in the amount of liquid reagent encapsulated.

On the other hand, a method is disclosed in which a freeze-dried solid reagent is placed in the cartridge, the blood sample is diluted with a dissolving diluent encapsulated in the cartridge, and the above described solid reagent is dissolved in the diluted sample solution, and is reacted therewith to carry out analysis (Published Japanese translation of PCT international publication for patent application No. 10-501340, Published Japanese translation of PCT international publication for patent application No. 9-504732 and the like).

In this method, the solid reagent is placed in chambers on the circumference located at the end of the channel in the cartridge, and the diluted sample is flown into each chamber to dissolve and react with the solid reagent, thus bringing about a change in absorbance. Also, since the liquid is fed by means of centrifugal force, the direction in which the liquid is fed is limited to the direction of the centrifugal force, namely a direction extending outwardly from the center of the circle of the circular cartridge.

As described above, for the detection reaction, only one reaction of one reagent composition can be carried out because the solid reagent is located at the end of the channel. Therefore, for some detection items, a reaction and reagent composition different from those of detection reactions specified in recommendations defined by academic societies and governmental agencies, which are conducted in medical laboratories and clinical laboratories of hospitals, must be employed. That is, in those recommendations, two or three types of reagent solutions are often used when one substance is detected (for example, described in Summary of Clinical Examination Process (written by Izumi Kanai, Kanahara press. 1998.), and if one type of reagent is used, correlation with previous examination data may be poor, and quantitation itself may be difficult to carry out.

Also, air in the above described chamber is pushed out by the inflow of a liquid, but since the chamber is located at the end of the channel, the air cannot be discharged from the cartridge, and should be moved to other location in the cartridge. Therefore, a design is made so that the above described air is let out through the upper space of the channel into which a liquid is flown. In other words, there is a disadvantage in terms of channel that the liquid and gas are flown in opposite directions in a very narrow channel.

A technique in which droplets of reagent solution are dropped in liquid nitrogen to be frozen in spherical forms, and are dried directly under a reduced pressure for dissolving in a short time the reagent placed in the chambers on the circumference is disclosed in International Patent Publication WO 93/04195, Published Japanese translation of PCT international publication for patent application No. 10-501340A and Published Japanese translation of PCT international publication for patent application No. 9-504732A.

In these documents, it is also disclosed that polyethylene glycol, myoinositol, polyvinyl pyrolidone, dextran, sodium cholate, mannitol, albumin or a mixture thereof is used as an adjuvant for forming droplets in good quantitation and enhancing solubility. Furthermore, it is described that glycerol is added in Example 3 of International Patent Publication WO 93/04195 (ALP Measurement Reagent), but its object is not been clarified.

A method is also disclosed in which the solid reagent deposited in the cartridge is dissolved in plasma being just a sample without using a sample dissolving liquid to carry out analysis. It is disclosed in, for example, Trade Name: Twinkle® of Nippon Medi-physics Co., Ltd., Japanese Patent Laid-Open No. 9-196920 (Immune Item), Japanese Patent Laid-Open No. 8-114539 (Biochemical Item), Japanese Patent Laid-Open No. 9-196739 (Dissolving Liquid Tip detection) and Japanese Patent Laid-Open No. 9-138195 (Analysis by Transmittance Optical measurement of Porous Material).

In this method, the solid sample is dissolved in plasma itself while a reaction is carried out at the same time, but it is not easy to dissolve uniformly a solid reagent using 100% plasma in a very short time. Also, there is the problem of vulnerability to contaminants (inhibiting substance) inhibiting analysis because the plasma is not diluted.

In these disclosed techniques, a method in which a liquid is suctioned under a reduced pressure from the end of the channel is employed as a principal method of feeding the liquid. In other words, a plurality of openings leading to the outside of the cartridge are provided in the direction of flow at a predetermined interval in one channel, and the feeding of the liquid is controlled by opening/closing the openings outside the cartridge. However, in this method of feeding the liquid, there is a disadvantage that the flow of the liquid can be controlled only linearly. These openings do not have the function of hydrophobic vents, but play a role as air release valves capable of reducing a pressure in the areas upstream of the openings by closing the openings.

In addition thereto, methods in which the reagent is deposited through the channel include those disclosed in U.S. Pat. No. 5,478,751 Specification (Abbott Co., Ltd.), Japanese Patent Laid-Open No. 3-223674 (Mochida Pharmaceutical Co., Ltd.) and U.S. Pat. No. 5,147,607 Specification (Mochida Pharmaceutical Co., Ltd.), and these method are not different from the above described methods in a sense that the sample is contacted with the reagent of high concentration and diluted in succession although substances to be flown through the channel are not necessarily 100% plasma. Those methods are used in the case where a solid phase antibody (antigen) is contacted with the sample as in immune-detecting reaction, but is not suitable for blood biochemical examination based on the reaction in a homogeneous system and examination of hazardous substances in the environment.

In addition, methods in which a filter paper or the like is impregnated with the analyzing reagent, the reagent is contacted with the blood sample, and the plasma is moved on the filter paper using the capillary force and gravity to carry out analysis have gone into actual use. These methods include, for example, those described in Spotchem® (trade name) manufactured by Kyoto Daiichi Kagaku Co., Ltd., Drychem® (trade name) manufactured by Fuji Photo Film Co., Ltd., Reflotron® (tradename) manufactured by Boehringer Mannheim K.K. or U.S. Pat. No. 5,212,065 (International Diagnostic System).

The so called analyzing filter paper based cartridges based on dry chemistry are convenient because they enable quantitative reaction while the reagent solution and buffer do not need to be added from the outside. However, the amount of required blood sample is large, namely about 10 µl for each item of analysis, which means that one hundred and a few ten µl of blood is required in the case of measurements for ten items or more that are usually conducted in the blood biochemical examination. Also, in association therewith, the amount of reagent used to impregnate the filter paper or the like is increased. Also, because the sample is contacted and reacted in succession with the reagent with which the filter paper or the like is impregnated, the type of analysis reactions is limited, and some of them are different from the aforesaid recommended methods defined by academic societies.

In addition, since the sample is not diluted, possibilities of being adversely influenced by contaminants in the sample are increased. Also, for the most part, one cartridge is required for each item of analysis, and only the method of Kyoto Daiichi Kagaku enables a plurality of analyses to be carried out at the same time, but in this method, essentially a plurality of cartridges each being used for one item of analysis are placed on the same strip, allowing only six items to be analyzed at the maximum.

On the other hand, in contrast to the above described methods using dry chemistry, the technique of µTAS (micro total analysis system) to carry out micro analysis has been developed. In the µTAS, for reducing the amount of any sample as well as blood to a very small level, a chip of a few to ten centimeter square with grooves provided on the surface of glass or silicone is used, and the reagent solution and sample are flowed in the groove to carry out separation and reaction to analyze a very small amount of sample (Japanese Patent Laid-Open No. 2-245655A, Japanese Patent Laid-Open No. 3-226666A, Japanese Patent Laid-Open No. 8-233778A, Analytical Chem. 69, 2626-2630 (1997) Aclara Biosciences, etc.). For this technique, there is an advantage that the amount of sample, the amount of reagent required for detection, the amount of wastes from consumable products used in detection and the amount of waste liquids are all reduced, and time required for detection can be shortened.

The inventors have also submitted applications related to the µTAS such as Japanese Patent Application No. 10-181586 specification ("Mixing analysis apparatus and mixing analysis method"), Japanese Patent Laid-Open No. 2000-2675A (Japanese Patent Application No. 10-181587 Specification "Capillary Photothermal Converting analysis apparatus"), Japanese Patent Laid-Open No. 2000-2677A (Japanese Patent Application No. 10-167603 Specification "Analysis apparatus"), and International Patent Publication WO 99/64846 (International Patent Application PCT/JP99/03158 Specification).

If the technique described in these specifications is used, the amount of reagent solution required for analyzing one item of blood biochemistry can be reduced to as small as about 10 nl, and the amount of sample required can be reduced to about 1 to 0.1 nl (1000 to 100 µl) with the detection time being about 10 seconds (About 1 µl of buffer for feeding the liquid entirely is required in addition thereto. Also, about 10 nl of sample may be required for 10 minutes if the sample is continuously fed).

However, in µTAS techniques that are now widely known, separation, mixture, reaction and detection are carried out within the chip (cartridge), but the reagent solution required for reaction is supplied from the outside of the chip (cartridge). Those techniques include, for example, those of prior arts related to the aforesaid µTAS, Proceedings of the µTAS '98 Workshop, held in Banff, Canada, 13-16 Oct. 1998. Editors: D. Jed Harrison and Albert van den Berg, Kluwer Academic Publishers and the like, and techniques of DNA analysis in a resin chip (R M Mccormick et al./Anal. Chem. Vol. 69, No. 14 (1997) 2626-2630, etc.).

These techniques are not suitable for the POC analyses and the like where simplicity is required, because a container for the liquid reagent needs to be provided outside the chip, maintenance operations for replenishing the liquid reagent, removing clogs or performing cleaning in the connection between the chip and the container are required.

On the other hand, for allowing the sample and the reagent solution to move in the chip (cartridge), air in the capillary (groove) leading to the destination to which they move needs to be discharged to the outside of the channel. At this time, it is desirable that a gas-permeable/non-liquid-permeable mechanism is provided at the end of the channel for surely keeping liquid in the chip. Otherwise, the liquid may be spilled out of the chip.

For achieving the purpose of providing this gas-permeable/non-liquid permeable mechanism, techniques in which small hydrophobic openings and hydrophobic membranes are used as vents through which not liquid but only air can be passed have been considered for rather a long time as techniques coping with a much larger amount of liquid compared to the case of the capillary.

For example, the technique of air vent from the blood in a blood processing apparatus such as an artificial dialyzer is described in Japanese Patent Laid-Open No. 57-17659A and Published Japanese translation of PCT international publication for patent application No. 9-500809A. Also, an example of providing vents in an apparatus much larger than the chip as automatic air vent filters for venting air in liquid chemicals and water that are used in factories in general is described in Japanese Patent Laid-Open No. 2-2812A. In any case, they cope with a much larger amount of liquid compared to an amount of liquid below the level of micro liters.

For those that are used as these air vents in the chip for coping with an amount of liquid below the level of micro liters, very small hydrophobic openings of about 3 µm square (HMCV (Hydrophobic Micro Capillary Vent)) are known (proceedings of the μTAS '98 Workshop, held in Banff, Canada, 13-16 Oct. 1998. Editors: D. Jed Harrison and Albert van den Berg, Kluwer Academic Publishers, p 307-310 Hydrophobic microcapillary vent for pneumatic manipulation of liquid in μTAS, Kazuo Hosokawa, Teruo Fujii, and Isao Endo, Document of Electricity Academy Workshop: Society for Study of Chemical Sensor System CS-99-1 to 12, p 19-22, Mar. 16, 1999, Teruo Fujii, Kazuo Hosokawa, Hong Jong Wook, Minoru Seki, Isao Endo et al.).

Also, a technique in which a hydrophobic membrane is provided at the end of the channel is disclosed (Affy Metrix Co., Ltd., Anderson et al., Proceeding of Transducers '97. 1997 International conference on Solid state sensors and Actuators 2C1. 02, International Patent Publication WO No. 9702357, U.S. Pat. No. 5,856,174 Specification). In this technique, the reagent solution and sample outside the chip are connected to the chip through a tube, a capillary through which the above described reagent solution and the above described sample are flown is selected with a diaphragm valve (valve opened/closed by force from the outside of the chip) provided in the chip. Then, the air in the capillary is pushed to the outside of the channel through the vents composed of a hydrophobic membrane at the end of the channel to feed the liquid. The above described vents always are opened outwardly, the feeding of the liquid is controlled by using pressure losses of the channel connected to the vents and providing pressure-relief openings with breakable seals, thus rising the problem of the structure being extremely complicated.

An object of the present invention is to solve the problems of conventional techniques as described above, and provide an analyzing cartridge as described below and a method for producing the same:

1) It is possible to prepare a reagent solution of a few μl or less in the cartridge at the time of measurement to provide the same for the reaction, which is difficult for the system in which the liquid is encapsulated in bags or chambers in the cartridge (liquid bag system), and is discharged into a reaction vessel at the time of measurement.

2) Measurements and reactions can be carried out using a very small amount of sample in the order of nanoliters to picoliters.

3) A reagent, buffer and the like required for analysis are encapsulated in the cartridge or attached thereto, and thus time and effort for management and maintenance of the reagents by an analysis operator can be alleviated or totally saved.

4) Analysis can be carried out conveniently, in a short time and inexpensively.

5) Limitations on the detection reaction are reduced, and analysis for multiple items can be carried out at the same time. Therefore, detection reactions the same as or similar to those of the recommended methods defined by academic societies, government agencies and the like can be carried out.

6) The analyzing cartridge has a simple internal structure and can thus be produced inexpensively.

7) The feeding of the liquid can be carried out accurately.

Another object of the present invention is to provide an analyzing method using the above described analyzing cartridge.

Still another object of the present invention is to provide a liquid feed control device that can be attached to the analyzing cartridge as described above, is capable of controlling the feeding of the liquid in the analyzing cartridge accurately and easily, and is inexpensive.

DISCLOSURE OF THE INVENTION

The present invention comprises the following configuration for achieving the above described objects. That is, the analyzing cartridge according to the present invention is an analyzing cartridge having a plurality of reservoirs, and capillaries connected for communication between these reservoirs, characterized in that at least one of the above described reservoirs is provided with openings leading to the outside of the analyzing cartridge, at least one of the openings is covered with gas-permeable/non-liquid-permeable vents, and the analyzing cartridge is provided therein with reagents for use in analysis.

The analyzing cartridge having such a configuration can be produced inexpensively because the structure in the cartridge is simple, and is capable of treating a very small amount of liquid as in the case of μTAS. Also, by controlling the access of the gas to the above described vents, the flow of the liquid into or from the above described reservoirs through the above described capillaries can be controlled, thus making it possible to control the flow of the liquid into and from each reservoir in the analyzing cartridge without supplying the liquid from the outside of the analyzing cartridge and taking the liquid out to the outside thereof.

Thereby, an all-in-one type analyzing cartridge requiring no maintenance, with all reagents and the like other than a sample encapsulated in the analyzing cartridge, can be provided. Also, the feeding of the above described liquid can be controlled accurately and easily.

In addition, if the analyzing cartridge has a configuration as described above, a part or all of reagents for use in analysis is provided in the analyzing cartridge, thus making it possible to reduce (or totally save) time and effort for management and maintenance of reagents conducted by an analysis operator at the time of analysis in POC analyses and the like. Also, the amounts of the sample and reagent required for analysis can be reduced to a very low level, and analysis can be carried out conveniently, in a short time and inexpensively.

Also, because limitations on the detection reaction are reduced, and analysis for multiple items can be carried out at the same time, detection reactions the same as or similar to those of the methods defined by academic societies and government agencies can be carried out in POC analyses and the like. Thus, a comparison with data obtained by clinical tests conducted in the past can be made easily. Furthermore, an analysis operator can encapsulate desired reagents in the above described analyzing cartridge to carry out a desired analysis.

Furthermore, at least one of the reservoirs provided with the above described openings covered with the above described vents can be provided with the above described reagents.

Also, at least one of the above described reagents can be a non-fluid reagent.

This configuration allows the above described non-fluid reagent to be dissolved in a reagent dissolving liquid or the like to prepare a reagent solution immediately before analysis in the above described analyzing cartridge, thus reducing possibilities that the reagent is spilled out from the above described analyzing cartridge during transportation and storage, and curbing degradation in quality of reagents, compared with the case where liquid reagents are encapsulated in reservoirs.

Also, because an analyzing cartridge with reagents encapsulated therein can be provided as a product, the analysis operator can conduct a desired analysis without carrying out operations for encapsulating reagents in the analyzing cartridge if an analyzing cartridge with desired reagents encapsulated therein is purchased.

Methods for encapsulating non-fluid reagents in the analyzing cartridge include a method in which a required amount of non-fluid reagent is encapsulated in the reservoir, and a method in which the reservoir is charged with a solution with a reagent dissolved therein, and is thereafter dried into a non-fluid reagent.

Furthermore, in the present invention, the non-fluid reagent refers to a solid reagent such as powders and freeze-dried products and a rubber-like reagent, and may be a glutinous starch syrup-like reagent having viscosity to prevent the reagent from being flown out from the analyzing cartridge during distribution (transportation, storage and the like) of the analyzing cartridge.

If this non-fluid reagent is encapsulated in a reagent storing reservoir provided with the above described vents to provide the same as a product, a reagent dissolving liquid encapsulated in or attached to the analyzing cartridge can be fed to the above described reagent storing reservoir through the above described capillary to dissolve the above described reagent immediately before analysis. Furthermore, since the above described reagent solving solution may be used in the amount of a few ten μl or so, and is quite inexpensive, it can be placed in the analyzing cartridge based on the liquid bag system.

For reducing the solution time during which the non-fluid reagent encapsulated in the analyzing cartridge is dissolved in the above described reagent dissolving liquid, an adjuvant for solution may be added in the non-fluid reagent for some measurement items. For this adjuvant for solution, polyol is suitable, and in particular, at least one type selected from ethylene glycol, propylene glycol and glycerol is preferable.

In addition, for the analyzing cartridge according to the present invention, the above described vent may be constituted by a hydrophobic member having pores. In particular, the member having pores is preferably a hydrophobic porous membrane.

In the case where the above described-openings of a plurality of reservoirs are covered with a common hydrophobic porous membrane to form the vents of each reservoir, the above described hydrophobic porous membrane should be in a state in which portions located between reservoirs do not have porosity. And, the above described hydrophobic porous membrane can be turned into the non-porous state by applying a pressure to the portions located between reservoirs.

In such a configuration, it is difficult for a gas to pass through the portions located between the above described reservoirs, and thus a gas is hardly flown between the above described reservoirs. Therefore, possibilities that the control of the access of the liquid to the adjacent reservoirs is adversely influenced are reduced, and thus its entry into/exit from each reservoir can be controlled independently and accurately.

Furthermore, the same goes for a reservoir group that is constituted by a plurality of reservoirs and for which the entry/exit of the liquid is carried out at a time. In other words, in the case where a plurality of reservoir groups are covered with a common hydrophobic porous membrane to form vents of each reservoirs, the above described hydrophobic porous membrane should be in a state in which the portions located between reservoir groups do not have porosity. Thus, the access of the liquid to reservoir groups can be controlled independently and accurately.

In addition, the analyzing cartridge according to the present invention comprises a sample storing reservoir for storing a liquid sample, a diluent storing reservoir for storing a diluent for diluting the above described sample, a measuring reservoir for measuring the above described sample, and a diluting reservoir for mixing the above described diluent with the above described measured sample to dilute the same, and may have a structure in which the above described capillary is connected for communication between the above described measuring reservoir and the above described sample storing reservoir, the above described diluent storing reservoir and the above described diluting reservoir, respectively.

Also, the analyzing cartridge according to the present invention comprises a calibration solution storing reservoir for storing a calibration solution for calibrating the result of analysis, and a sample storing reservoir for storing a liquid sample, a diluent storing reservoir for storing a diluent for diluting the above described calibration solution and the above described sample, a measuring reservoir for measuring the above described calibration solution and the above described sample, and a diluting reservoir for mixing the above described measured calibration solution or the above described measured sample with the above described diluent to dilute the same, and may have a structure in which the above described capillary is be connected for communication between the above described measuring reservoir and the above described calibration solution storing reservoir, the above described sample storing reservoir, the above described diluent storing reservoir and the above described diluting reservoir, respectively.

Furthermore, as described above, the above described various kinds of reservoirs communicate with each other by the above described capillary, but the above described various kinds of reservoirs may communicate with each other directly by the above described capillary, or may communicate with each other indirectly in such a manner that other reservoirs exist between reservoirs. However, they preferably communicate with each other directly, in consideration with accuracy and efficiency in control of the entry/exit of the liquid.

In addition, the all-in-one type analyzing cartridge of the present invention as described above may be produced by a method comprising a plane processing step of providing through-holes at the positions corresponding to the above described reservoirs of a plane member and providing grooves at the positions corresponding to the above described capillary of one plate face of the plane member, a vent forming step of covering with the above described vent the plate face of the above described plane member that does not have the above described groove, a reagent introducing step of introducing the above described reagent into the above described through-hole corresponding to the reagent storing reservoir for storing the above described reagent, from the plate face of the above described plane member having the above described groove, and a covering step of covering with a cover sheet the plate face of the above described plane member having the above described groove to form the above described reservoir and the above described capillary.

Here, the above described vent forming step may be changed to a step of covering the plate face of the above described plane member that does not have the above described groove with a hydrophobic member having the above described pores or the above described hydrophobic porous membrane. Also, the above described reagent introducing step may be changed to a step of introducing a solution of the above described reagent into the through-hole corresponding to the reagent storing reservoir for storing the above described reagent from the plate face having the above described groove, and drying the solution of the reagent into a non-fluid reagent.

Furthermore, usually, the above described groove is provided only in one plate face of the above described plane member, and the other plate face that does not have the above described groove is covered with the above described vent.

In addition, the liquid feed control device according to the present invention is a liquid feed control device that is attached to an analyzing cartridge as described above to control the feeding of the liquid between the above described reservoirs via the above described capillary, characterized in that the above described liquid is flown into the above described reservoir via the above described capillary or is flown out from the above described reservoir by allowing or regulating the entry/exit of the gas via the above described vents.

Due to this configuration, the liquid feed control device is capable of controlling accurately the feeding of liquids such as a sample, a reagent solution and the like in the above described analyzing cartridge, and can be produced inexpensively.

In addition, the liquid feed control device according to the present invention may comprise valves placed in the positions opposite to the above described reservoirs with the above described vents therebetween, in which the entry/exit of the gas via the above described vents is allowed or regulated by the valves. Alternatively, the liquid feed control device may comprise couplers placed in the positions opposite to the above described reservoirs with the above described vents therebetween, and attached to the above described vents in such a manner as to cover the above described openings, pumps coupled to the above described couplers, and valves placed between the above described couplers and the above described pumps, in which the entry/exit of the gas via the above described vents is allowed or regulated by at least one of the above described pump or the above described valve.

In addition, the liquid feed control device according to the present invention may control the outflow of the above described liquid from the above described reservoirs via the above described capillary by allowing or regulating the access of the gas to the above described reservoirs with the above described openings not covered with the above described vents.

Furthermore, this liquid feed control device may be combined with a detection device for analysis, or may be independent thereof.

In addition, the analysis method according to the present invention is a method for analyzing a sample using an analyzing cartridge as described above, characterized by comprising a reagent dissolving step of feeding a reagent dissolving liquid from a reagent dissolving liquid storing reservoir in which the above described reagent dissolving liquid for dissolving the above described non-fluid reagent is stored to the reagent storing reservoir in which the above described non-fluid reagent is stored through the above described capillary immediately before analysis to dissolve the above described reagent to prepare a reagent solution.

Furthermore, the analysis method may comprise a mixing and reacting step of mixing and reacting together the above described liquid sample and the above described reagent solution in the above reagent storing reservoir using the above described capillary.

In addition, the analysis method according to the present invention is a method of analyzing a sample using an analyzing cartridge as described above, characterized by comprising a step of feeding a sample to the measuring reservoir to measure the sample, and feeding a diluent and the measured sample to the diluting reservoir to mix the same to dilute the above described sample.

In addition, the analysis method according to the present invention is a method of analyzing a sample using an analyzing cartridge as described above, characterized by comprising a step of feeding a sample to the measuring reservoir to measure the sample, and feeding a diluent and the measured sample to the diluting reservoir to mix the same to dilute the above described sample, and a sample analyzing step of mixing this diluted sample with the reagent, followed by analyzing the same, and comprising before and after the above described sample analyzing step, a step of diluting and analyzing a calibration solution using the measuring reservoir and the diluting reservoir that will be used or have been used for dilution of the above described sample, and calibrating the value measured by analysis of the sample using the value measured by analysis of the calibration solution. Furthermore, hereinafter, the above described calibration solution is referred to also as a standard solution.

BRIEF DESCRIPTION OF THE DRAWINGS

FIG. 3 illustrates a situation in which a portion pack with a liquid encapsulated therein is broken to introduce the contents into the reservoirs of the analyzing cartridge;

FIG. 10 shows a laboratory device for measuring the antiwater pressure of a hydrophobic membrane;

FIG. 11 shows the channel pattern of the plane member constituting the analyzing cartridge of one embodiment of the present invention;

BEST MODE FOR CARRYING OUT THE INVENTION

Figure 1:
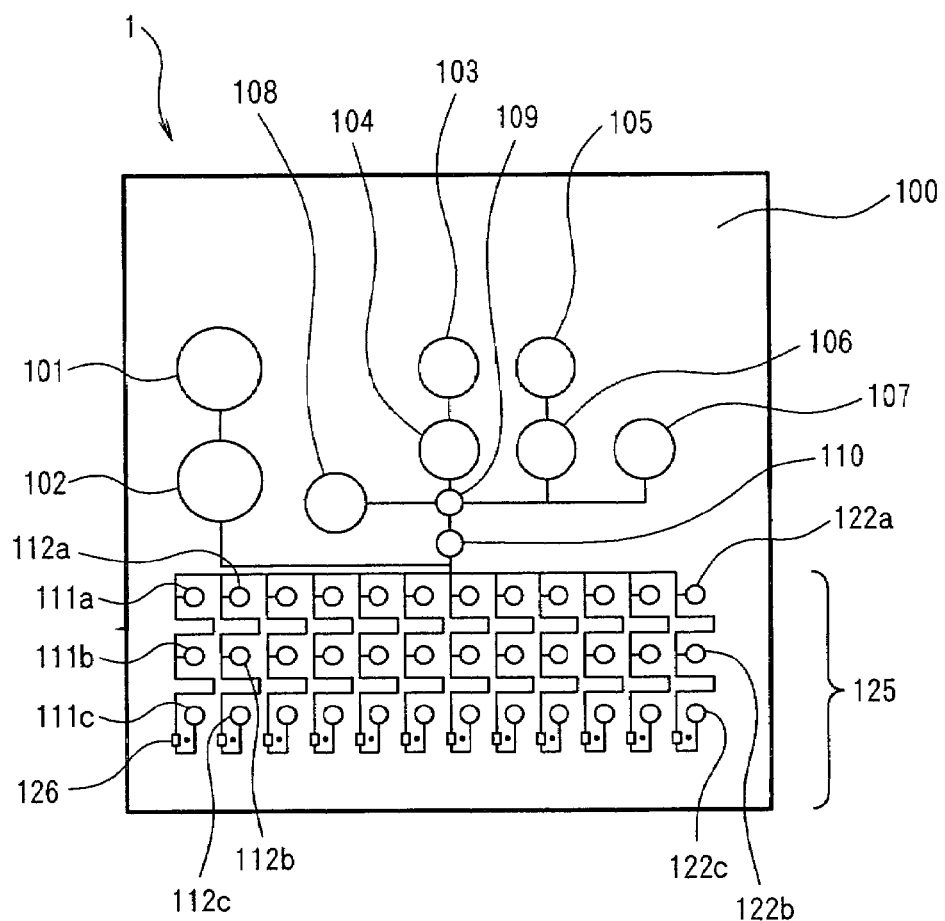
FIG. 1 shows a channel pattern of an analyzing cartridge when a biochemical item of clinical diagnosis is measured.

Embodiments of an analyzing cartridge and a liquid feed control device according to the present invention will be described in detail referring to the drawings. However, the present invention should not be limited to the embodiments. Particularly, for methods of feeding the liquid in the analyzing cartridge, a method in which the feeding of the liquid is controlled by means of air pressure has principally been described, but the method is not limited thereto, but may be a method of feeding the liquid using electroosmotic flows and a method of feeding the liquid using gravity as drive force, or may be a method in which vents of reservoirs are deformed (pushed) from the outside to feed the liquid.

Furthermore, terms indicating directions such as "upper", "down", "front", "back", "left" and "right" mean individual directions in each drawing for the sake of convenience in explanation.

Figure 2:
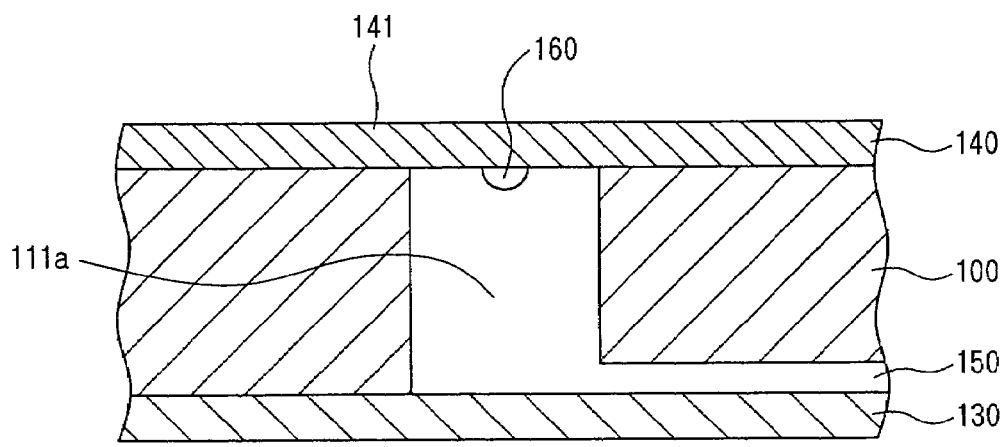
FIG. 2 is a partial sectional view of a reservoir portion of the analyzing cartridge of FIG. 1.

FIGS. 1 and 2 show an analyzing cartridge 1 (for measurement of chemical items of clinical diagnosis) of the first embodiment of the present invention. FIG. 1 shows a channel pattern of the analyzing cartridge 1, and is a view taken from the side of the surface of a plane member 100 constituting the analyzing cartridge 1 that does not have grooves. Also, FIG. 2 is a partial vertical sectional view of a reservoir portion of the analyzing cartridge 1. Furthermore, FIG. 2 shows as a representative example a reagent storing reservoir 111a of various kinds of reservoirs.

The analyzing cartridge 1 has the plane member 100 formed by a material selected from organic polymers such as PMMA, silicon, glass and the like, this plane member 100 is provided with a large number of through-holes 101 to 108, 110 to 122c pierced through the member from the front face to the back face, and the back face of the plane member 100 is provided with a large number of grooves with widths and depths being a few μm to a few mm (shown by lines in FIG. 1).

That is, a through-hole 101 having a relatively large diameter is provided in the slightly upper position on the left side, and a through-hole 102 having a relatively large diameter is provided below the through-hole 101, and a groove is provided in such a manner as to make a link between the through-holes 101 and 102.

Also, a though-hole 103 having a medium size diameter is provided in the slightly upper position nearly at the center of the member, a through-hole 104 having a medium size diameter is provided below the through-hole 103, a through-hole 105 having a medium size diameter is provided on the right side of the through-hole 103, a through-hole 106 having a medium size diameter is provided below the through-hole 105, and a through-hole 107 having a medium size diameter is provided on the right side of the through-hole 106. And, a groove is provided in such a manner as to make a link between the through-holes 103 and 104, and a groove is provided in such a manner as to make a link between the through-holes 105 and 106.

Also, a through-hole 108 having a medium size diameter is provided on the right side of the through-hole 102, and a wide groove 109 that is wider than other grooves is provided on the right side of the through-hole 108 and below the through-hole 103. And, grooves are provided in such a manner to make links between the wide groove 109 and the through-hole 103 and between the wide groove 109 and the through-hole 108, respectively, and links are made between the wide groove 109 and the through-holes 106 and 107 by grooves branched at some midpoints thereof.

In addition, a through-hole 110 having a small diameter is provided below the wide groove 109, and a groove is provided in such a manner as to make a link between the wide groove 109 and the through-hole 110. And, a short groove extending downward from the through-hole 110 is provided, and a groove extending downward from the through-hole 102 and bending in the right direction is connected to the short groove.

And, in the lower part of the plane member 100, a large number of through-holes are provided in such a manner that through-holes are arranged in a plurality of rows in the vertical direction and in a plurality of columns in the lateral direction. In FIG. 1, the plane member 100 in which total 36 through-holes with 3 rows in the vertical direction and 12 columns in the lateral direction 111a, 111b, 111c, 112a, 122a, 122b, 122c are provided is shown as an example.

These through-holes 111a to 122c are through-holes having diameters further smaller than that of the through-hole 110, and three through-holes (111a, 111b and 111c, etc.) in each column constitute one group, and each group has the same configuration.

And, the short groove extending downwardly from the through-hole 110 is branched into a bunch of a large number of grooves, and each of the branched grooves extends downward on the left side of each group consisting of the above described three through-holes (111a, 111b and 111c, etc.), is bent in a U-shaped form between the first row of through-holes 111a, 112a, . . . , 122a and the second row of through-holes 111b, 112b, . . . , 122b and between the second row of through-holes 111b, 112b, . . . , 122b and the third row of through-holes 111c, 112c, . . . , 122c, and is connected to the third row of through-holes 111c, 112c, . . . , 122c from the lower side in a roundabout way. Furthermore, the groove bent in a U-shaped form may be a linear groove, a curved groove or the like as long as it is long enough to allow the liquid to be flown for a time period required for mixture and reaction of the sample and reagent.

Also, the through-holes 111a, 112a, . . . , 122a in the first row and the through-holes 111b, 112b, . . . , 122b in the second row are each connected through grooves extending therefrom toward the left to grooves extending vertically on the left side of each group.

Furthermore, the diameters of the above described through-holes 101 to 108, 110 to 122c may be different for the front face and the back face of the plane member 100 (i.e. tapered through-holes), or may be the same. Also, the through-holes 101 to 108, 110 to 122c may be provided in the plane member 100 using a drill, laser or the like after formation of the plane member 100, or if the plane member 100 is made of resin, the mold for forming the plane member 100 may be provided in advance with raised portions for provision of the through-holes 101 to 108 and 110 to 122c to provide the through-holes at the time when the plane member 100 is formed.

On the other hand, a plane cover sheet 130 is bonded to the back face of the plane member 100 provided with the above grooves as shown in FIG. 2, and thereby the above described groove is a capillary 150. Also, the above described through-holes 101 to 108 and 110 to 122c have on the front face of the plane member 100 openings leading to the outside of the plane member 100, and work as reservoirs in which liquids such as a sample and reagents and waste liquids can be stored. Furthermore, the symbols 101 to 108 and 110 to 122c used for specifying through-holes will also be used directly as symbols for reservoirs, hereinafter, for the sake of explanation and illustration.

And, a membrane 140 through which the liquid cannot be passed but the gas (particularly air) can be passed (e.g. PTFE porous membrane) is bonded to the front face of the plane member 100, and thereby a vent 141 covering the openings of the reservoirs 102, 104, 106, 108 and 110 to 122c is formed.

Now, the uses of reservoirs 101 to 108 and 110 to 122c and the wide groove 109 will be described briefly (they will be described in detail later).

The reservoirs 101 and 102 are reservoirs for a reagent dissolving liquid (hereinafter described as reagent dissolving liquid dropping reservoir 101 and reagent dissolving liquid storing reservoir 102), the reservoirs 103 and 104 are reservoirs for a sample diluent (hereinafter described as sample diluent dropping reservoir 103 and sample diluent storing reservoir 104), and the reservoirs 105 and 106 are reservoirs for a standard solution (hereinafter described as standard solution dropping reservoir 105 and standard solution storing reservoir 106).

Also, the reservoir 107 is a reservoir for a sample (hereinafter described as sample storing reservoir 107), the wide groove 109 is a groove for measurement of sample and standard solution (hereinafter described as measurement vessel 109), the reservoir 10.8 is a reservoir for the waste liquid of the measurement vessel 109 (hereinafter described as waste liquid storing reservoir 108), and the reservoir 110 is a reservoir for diluting a sample with a sample diluent (hereinafter described as diluting and mixing vessel 110).

In addition, a total of 36 reservoirs 111a, 111b, 111c, . . . , 122c in the lower part of the plane member 100, in which 24 reservoirs in the upper two rows are reservoirs for the reagent (hereinafter described as reagent storing reservoirs 111a to 122a and 111b to 122b), and 12 reservoirs in the lower row are reservoirs for waste liquids (hereinafter described as waste liquid storing reservoirs 111c to 122c), form a quantitative reaction zone 125.

The form of encapsulation of the reagent in the analyzing cartridge 1 includes a form in which a non-fluid reagent 160 is fixed in the reservoir as shown in FIG. 2, and a form in which a portion pack 300 with a liquid sample 302 encapsulated therein is provided along with a pin 301 for breaking the portion pack 300 as shown in FIG. 3.

Furthermore, FIG. 3 illustrates a situation in which the portion pack 300 provided in the plane member 100 is pushed by a piston 303 from the outside of the plane member 100, whereby the portion pack 300 is broken by the pin 301 included therein outside the plane member 100 to let the liquid reagent 302 flow into the reagent dissolving liquid dropping reservoir 101 and the capillary 150.

The shape of the portion pack 300 that is used here is not particularly limited as long as it is a container capable of containing an amount of reagent dissolving liquid or diluent sufficient to dissolve or dilute the reagent and sample, but a box type or cylindrical pack that can easily be formed is preferable.

The material of the portion pack 300 preferably has excellent gas barrier properties so as to prevent transpiration of water in the contained liquid and degradation of the contained liquid due to entry of oxygen. For preventing entry of oxygen, a resin sheet on which aluminum is coated or deposited may be used, but the problem of entry of oxygen can be eliminated if the analyzing cartridge is wrapped tightly with nitrogen encapsulated therein. Also, preferably, transpiration of water is reduced as much as possible because the concentration of the contained liquid is changed if water is transpired. In particular, the portion pack in which the calibration solution is encapsulated, the amount of water transpiration should be as small as 0.1% per year, and an aluminum coated polyethylene sheet or the like is used.

For the material of the portion pack 300, resins of polyethylene, polypropylene, polyvinyl chloride, polycarbonate, polymethylpentene and the like are suitable as the material of the portion bag 300, because for these resins, permeability to water is reduced and injection molding and press molding can easily be applied.

Also, the portion pack 300 is preferably formed as thinly as possible so that it can easily be broken at the time of use. A reagent dissolving liquid or diluent is put in the formed portion pack, and a lid provided with a pin for breaking the portion pack is bonded thereto. The material of the lid and pin may be identical to or different from that of the portion pack. Also, the pin may be formed in such a manner that it is combined with the lid as one united body, or may be attached to the lid after it is formed. In any case, the pin should have such strength to break the bottom of the portion pack.

The lid provided with the pin is bonded to the portion pack by means of ultrasonic bonding, adhesion with an adhesive, bonding with a double-faced adhesive tape and the like. Also, the entire portion pack may be encapsulated in the analyzing cartridge, with the upper part thereof covered with the hydrophobic vent. In this case, the pin is not necessarily required, and the portion pack is broken with a pressure caused by pressing a piston or the like from over the vent to discharge the contained liquid.

For the shape of the portion pack, a piston-type container having a shape like a syringe is also used, in addition to the above described bag shaped portion pack. This piston-type container is provided at the outlet of contents with a tap that is broken or opened by application of a predetermined level of pressure, and when the piston-type container is attached to the analyzing cartridge with a liquid encapsulated in the container, and an inner cylinder (piston) is pressed from the outside by a device for controlling the feeding of the liquid and so on at the time of analysis, the contained liquid is pushed out from the above described outlet. Furthermore, the packing of the cylinder should be robust.

Also, a straw-like container composed of polyethylene or the like with one end closed is one example of inexpensive portion packs. In this container, when a pressure is applied to the container with a liquid encapsulated therein, the tap of the outlet is opened so that the contained liquid is pushed out to the reservoir and channel.

A liquid reagent required in a relatively large volume (a liquid of which amount is in the range of from a few ten to a few hundred μl, or a few thousand μl in some circumstances) such as a reagent dissolving liquid and sample diluent is encapsulated in this portion pack 300, which is then placed in the analyzing cartridge 1.

If the non-fluid reagent 160 is stuck, the above described non-fluid reagent 160 is dissolved in the reagent dissolving liquid supplied when the portion pack 300 is broken, so that a reagent solution is prepared in the analyzing cartridge 1.

If the portion pack 300 is used to introduce a reagent solution or the like into the reservoir, a reagent solution and buffer in predetermined concentrations may be placed in the portion pack 300. Also, for dissolving the non-fluid reagent 160 to prepare a reagent solution in a predetermined concentration in the analyzing cartridge 1, the reservoir needs to have a predetermined volume having a predetermined permissible variation range. In the case of blood biochemical examination, the variation of the concentration of the reagent after it is dissolved is preferably 2% or smaller as a CV value (value obtained by dividing a standard deviation by an average value). Therefore, the accuracy in formation and production of the reservoir and the accuracy in the process for bonding the cover sheet 130 and a venting membrane 140 become important. However, since there may be cases where the above described CV value becomes about 5% in the groove and reservoir in this embodiment due to variation of the accuracy in formation and production and the accuracy in processes, each analyzing cartridge is preferably calibrated using a standard solution.

Also, FIG. 2 shows an example of the case where the non-fluid reagent 160 is stuck to the venting membrane 140, but the non-fluid reagent may be stuck to the wall of the reservoir 111a as long as the entire surface of the capillary 150 and venting membrane 140 is not covered with the reagent. The reagent may be stuck to both the venting membrane 140 and the wall of the reservoir 111a as a matter of course.

Figure 4:
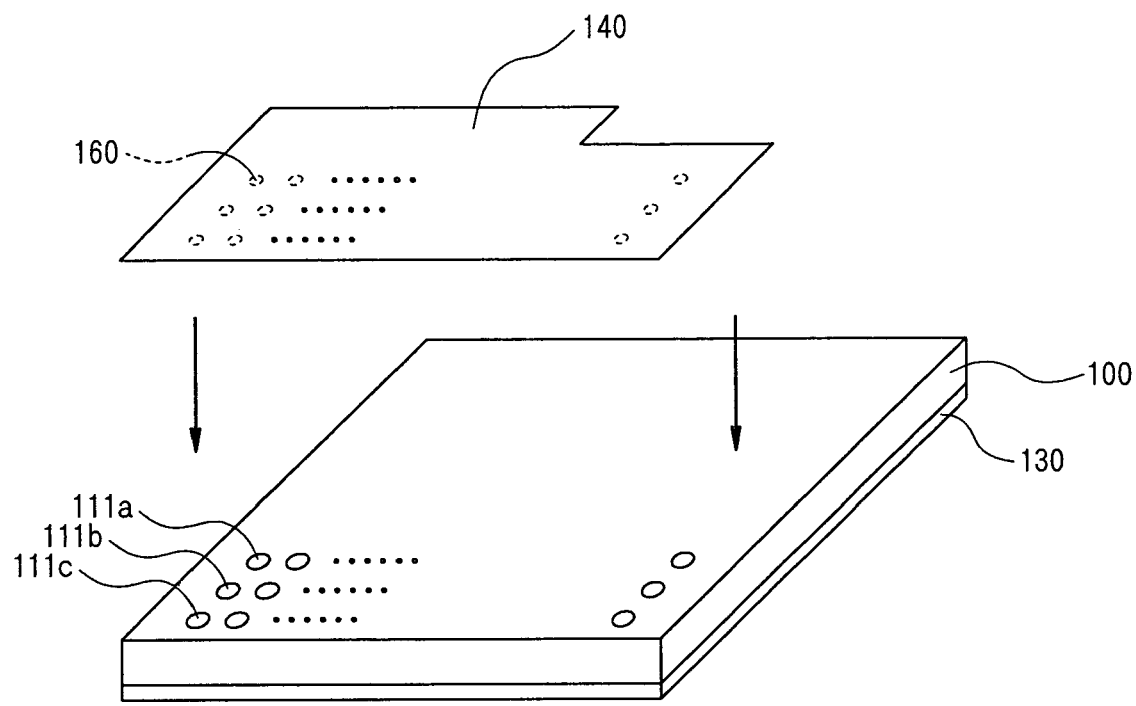
FIG. 4 illustrates a process for bonding a membrane with a non-fluid reagent stuck thereto to a plane member with the above described reagent therebetween as a vent.
Figure 5:
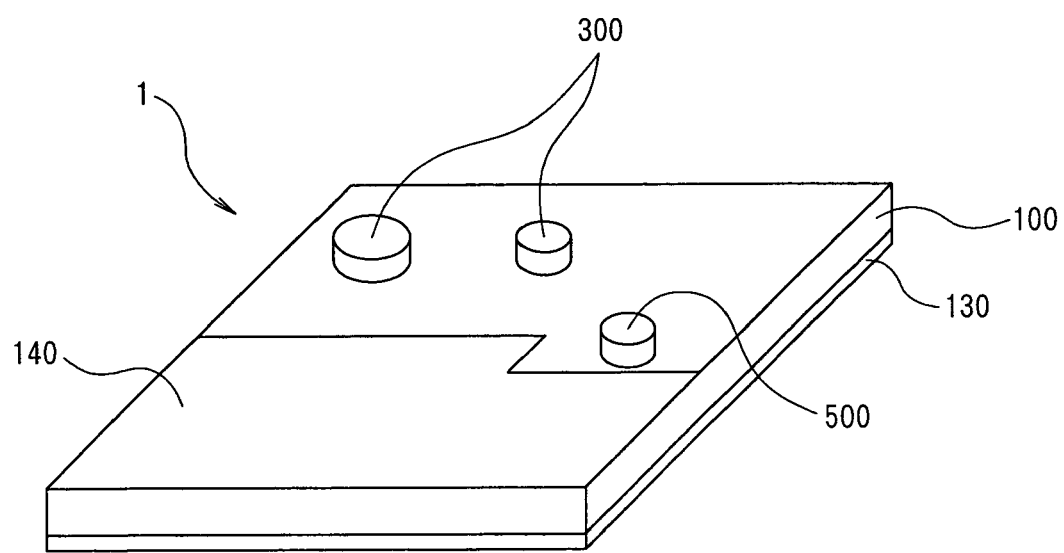
FIG. 5 is a perspective view showing the external appearance of the analyzing cartridge prepared through the process shown in FIG. 4.

FIG. 4 illustrates a process where the venting membrane 140 (e.g. PTFE porous membrane) with the non-fluid reagent 160 stuck thereto is bonded to the plane member 100 having through-holes 111a, 111b, 111c, . . . , 122c (FIG. 4 shows only some of the through-holes for convenience) constituting reservoirs, which has been produced by injection molding of an organic polymer, with the face bearing reagent 160 therebetween. And, FIG. 5 is a perspective view showing the external appearance of the analyzing cartridge 1.

As shown in FIG. 4, the non-fluid reagent 160 is stuck as spots in positions relative to the positions of the through-holes 111a, 111b, 111c, . . . , 122c on the venting membrane 140, and the non-fluid reagent 160 is encapsulated in the reservoirs 111a, 111b, 111c, . . . , 122c by bonding the venting membrane 140 to the plane member 100.

The plane member 100 with the cover sheet 130 bonded thereto has only a sample inlet 500 provided with a plasma separating filtration membrane for the opening for the liquid to pass through, and the reagent solving solution, the sample diluent and other reagents contained in the portion pack 300 are all encapsulated in the analyzing cartridge 1.

The feeding of the liquid in the capillary of the analyzing cartridge 1 of this embodiment is carried out by the liquid feed control device attached to the analyzing cartridge 1, using the vent 141. The liquid feed control device comprises a valve (not shown) for allowing or regulating the entry/exit of the gas via the vent 141. And, the valve is placed in the position opposite to the reservoir with the vent 141 therebetween, and is located between a coupler (not shown) tightly adhered to the analyzing cartridge 1 with the vent 141 covered therewith and an air pressure pump (not shown) Furthermore, the above described valve may be provided in the coupler.

That is, the above described liquid feed control device comprises a liquid feed control mechanism allowing the inflow of the liquid into the reservoir by opening the above described valve to allow access of the gas to the vent 141, and regulating the inflow of the liquid into the reservoir by closing the above described valve to regulate access of the gas to the vent 141.

For allowing the access of the gas via the vent 141, the coupler may be separated from the analyzing cartridge 1 to release the vent 141 directly into the outside, or a three-way valve may be used to release the vent 141 directly to the outside by switching the valve, with the coupler adhered to the analyzing cartridge 1. In addition, instead of the air pressure pump, a vacuum pump may be used to reduce the pressure in the coupler to a negative pressure. Furthermore, it is also possible to apply pressure to the liquid sending side and reduce a pressure in a liquid accepting side.

Also, the regulation of the access of the gas via the vent 141 may be carried out by adhering the coupler to the analyzing cartridge 1, and closing the above described valve, or stopping the air pressure pump.

Furthermore, the access of the gas via the vent 141 may be allowed or regulated using a liquid feed control device that carries out the operation without using the above described valve.

Such liquid feed control devices include, for example, a liquid feed control device that is provided on the side opposite to the reservoir of the vent with a coupler that is opened when a tube or the like coupled to the air pressure pump is attached thereto, and is closed when it is detached, and the allowing or regulating of the access of the gas via the vent is controlled by attaching/detaching the tube or the like.

Figure 6:
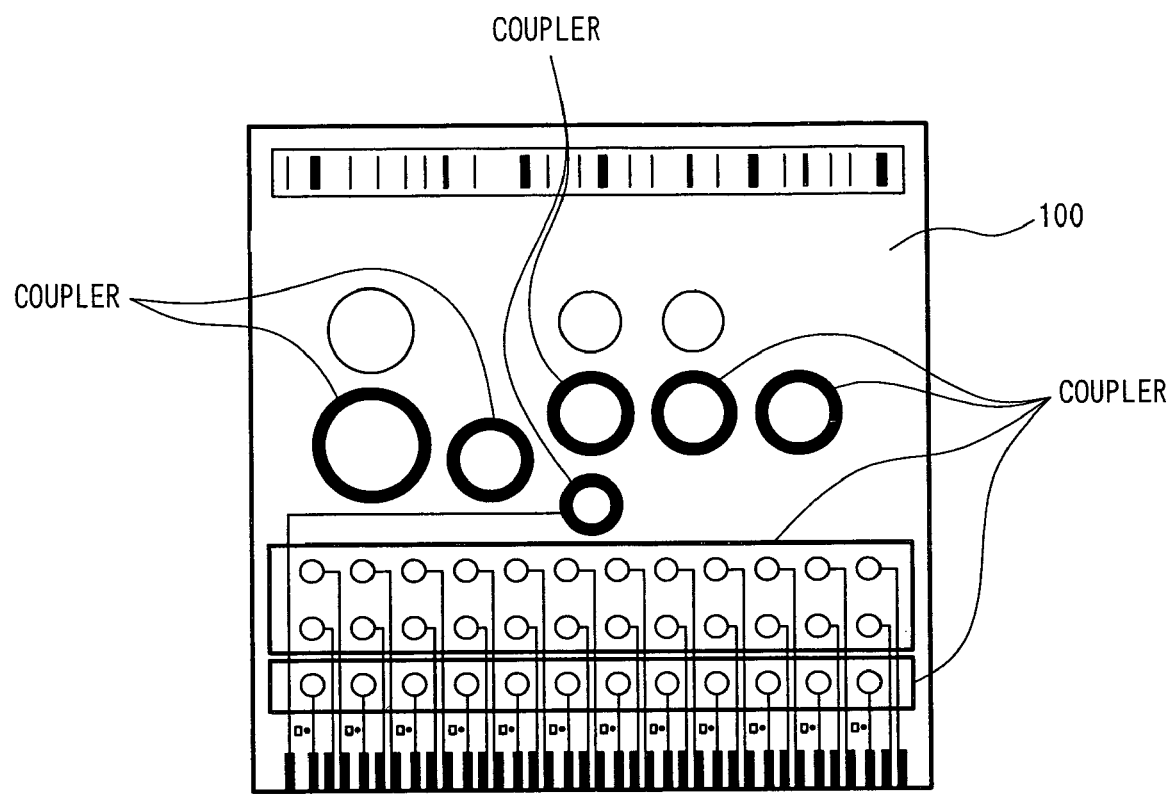
FIG. 6 shows one example of the position in which couplers are mounted in the plane member having the channel pattern of FIG. 1.

FIG. 6 shows one example of the position in which the coupler is provided in the plane member 100 of FIG. 1. As shown in FIG. 6, all reservoirs other than the reagent dissolving liquid dropping reservoir 101, the sample diluent dropping reservoir 103 and the standard solution dropping reservoir 105 are provided with the coupler.

Furthermore, for the reagent storing reservoir and the waste liquid storing reservoir, one coupler is provided in such a manner as to cover all the reagent storing reservoirs 111a, 112a, 113a, . . . , 122a, 111b, 112b, 113b, . . . , 122b, and one coupler is provided in such a manner as to cover all the waste liquid storing reservoirs 111c, 112c, 113c, . . . , 122c.

Also, in the example of FIG. 6, electrodes and wirings for feeding liquids by means of electroosmotic flows, and barcodes in which per-lot calibration values and measurement item information for the analyzing cartridge 1 are recorded are shown together.

Movements of liquids will now be described using FIG. 1 and FIG. 3. FIG. 3 is a view in which the analyzing cartridge 1 is set in an analysis apparatus, in which only a portion where the portion pack 300 is attached is shown for the analyzing cartridge 1, and only the piston 303 is shown for the analysis apparatus. Furthermore, this analysis apparatus may be combined with the liquid feed control device and detection device, or may be independent thereof.

This analysis apparatus has a mechanism in which the portion pack 300 attached to the analyzing cartridge 1 is pressed by the piston 303 provided in the analysis apparatus, whereby the contained liquid is discharged into the analyzing cartridge 1. More particularly, the piston 303 having a diameter matching the diameter of the portion pack 300 is placed in the portion where the portion pack 300 of the analyzing cartridge 1 is positioned, and at the beginning of analysis, the piston 303 automatically applies pressure to the portion pack 300 to make the reagent dissolving liquid or the sample diluent encapsulated in the portion pack 300 flow into the reservoirs of the analyzing cartridge 1.

That is, as shown in FIG. 3, the portion pack 300 with the reagent dissolving liquid contained therein is broken by pressing the same with the piston 303 to introduce the reagent dissolving liquid into the reagent dissolving liquid storing reservoir 102 via the reagent dissolving liquid dropping reservoir 101. At this time, the valve coupled to the coupler attached to the reagent dissolving liquid storing reservoir 102 is opened, and all other valves are closed. The amount of liquid in the portion pack 300 should be well larger than the volume of the reagent dissolving liquid storing reservoir 102 plus the reagent dissolving liquid dropping reservoir 101.

Similarly, the sample diluent is introduced from the portion pack 300 with the sample diluent contained therein into the sample diluent storing reservoir 104 via the sample diluent dropping reservoir 103.

If required, a standard solution with a detection object dissolved therein in a predetermined concentration (positive control) is introduced from the portion pack 300 into the standard solution storing reservoir 106 via the standard solution dropping reservoir 105 to allow for calibration. The standard solution is diluted using the measurement vessel 109 and the diluting and mixing vessel 110 identical to those for the sample. Calibration is carried out with the standard solution for each analyzing cartridge, whereby variations of the accuracy in the formation of the analyzing cartridge and the accuracy in the processing of the analyzing cartridge can be corrected, thus making it possible to carry out analysis of high accuracy.

In the reagent storing reservoirs 111a to 122a and 111b to 122b of the quantitative reaction zone 125 (qualitative reaction is also possible as a matter of course), the non-fluid reagent 160 of different composition suitable for each measurement is fixed. If the valves of the reagent storing reservoirs 111a to 122a and 111b to 122b each containing the non-fluid reagent 160 are opened, and pressure is applied to the reagent dissolving liquid storing reservoir 102 by the air pressure pump (not shown), and the valves of all other reservoirs are closed, the reagent dissolving liquid flows into each reagent storing reservoir 111a to 122a and 111b to 122b to dissolve the non-fluid reagent 160.

If the vent 141 has a predetermined performance, the air in each reagent storing reservoir 111a to 122a and 111b to 122b is discharged through the vent 141 to the outside of the analyzing cartridge 1, and when the reagent storing reservoirs 111a to 122a and 111b to 122b are filled with the liquid, the feeding of the liquid to the reagent storing reservoirs 111a to 122a and 111b to 122b is stopped. That is, each non-fluid reagent 160 is dissolved in the reagent dissolving liquid of which amount is consistent with the volume of the reagent storing reservoir to form a reagent solution in a predetermined concentration.

The total blood sample is introduced into the sample storing reservoir 107 through the plasma separation filtration membrane (filter). Then, the blood cell is filtered (the platelet may remain) to leave the plasma, which is stored in the sample storing reservoir 107. When the plasma sample in the sample storing reservoir 107 is flown into the measurement vessel 109, only the valve of waste liquid storing reservoir 108 is opened, and all other valves are closed.

And, when pressure is applied to the sample storing reservoir 107 with the above described air pressure pump, the plasma sample in the sample storing reservoir 107 flows into the waste liquid storing reservoir 108 through the measurement vessel 109 having a predetermined volume. If the valve of the waste liquid storing reservoir 108 is dosed at the time when the measurement vessel 109 is filled with the plasma sample, the feeding of the plasma sample is stopped. If the application of pressure to the sample storing reservoir 107 is stopped to close the valve, and then pressure is applied to the diluent storing reservoir 104 with the above described air pressure pump to open the valve of the diluting and mixing vessel 110, the plasma sample in the measurement vessel 109 is diluted with a diluent from the diluent storing reservoir 104 and flows into the diluting and mixing vessel 110.

Furthermore, after the reservoir is filled with the liquid, the valve is closed to stop application of pressure by the air pressure pump, but a system may be adopted in which the valve is automatically stopped by means for detecting that the air is no longer discharged from the vent, and soon. Then, application of pressure by the air pressure pump is stopped as soon as the reservoir is filled with the liquid, thus reducing the load on the vent.

A two-or-more-stage vessel is used as the diluting and mixing vessel 110 to carry out operations in a way as described above one after another, whereby mixing efficiency can be enhanced, or a two-stage diluting and mixing vessel is used to make the liquid go and return (make the liquid go and come back), whereby mixing efficiency can be enhanced. The dilution rate is uniquely determined by the volume of the diluting and mixing vessel 110 and the volume of the measurement vessel 109.

This volume is preferably calibrated by performing a spot check of the analyzing cartridge 1 for each lot of processing and assembly of the analyzing cartridge 1. Preferable is a system in which information of such calibration is recorded in the analyzing cartridge 1 by a barcode and a magnetic tape, and the analysis apparatus automatically reads the information at the time of measurement to calculate a value measured by analysis.

If the plasma sample diluted in a predetermined dilution ratio obtained in this way is reacted with a reagent solution in a predetermined concentration, the reaction for analysis such as a quantitative reaction, qualitative reaction and the like can easily be carried out in the analyzing cartridge 1.

The reagent solution in the reagent storing reservoirs 111a and 111b is reacted with the diluted sample one after another, and is measured in a detection portion 126 (detection by a thermal lens in the example in FIG. 1) before it flows into the waste liquid storing reservoir 111c in FIG. 1. The reagent storing reservoirs 112a and 112b and the waste liquid storing reservoir 112c are reservoirs for another measurement, and the reagent storing reservoirs 122a and 122b and the waste liquid storing reservoir 122c are reservoirs for still another measurement. Although symbols are not shown in the figure, the same goes for the other quantitative reaction zone 125.

For mixing in the analyzing cartridge 1, ratio of flow rates control system, as described below, in which the reagent solution and the diluted sample are consecutively mixed together at a predetermined ratio of flow rates to achieve a mixing ratio suitable for the reaction without carrying out measurements in terms of volume can be adopted. Also, each reagent solution is weighed in a way of measurement in the measurement vessel, and is mixed and subjected to quantitative reaction.

For the method of feeding the liquid between any reservoirs via the capillary, any one of the method based on a suction and exhaust pump as described above, the method based on gravity, described in Japanese Patent Application No. 11-352445 Specification by the inventor (not published when the application of the present invention is submitted), a method using electroosmotic flows as describe later, a method in which the liquid in the analyzing cartridge is pushed or pulled from the outside via a partition wall with a piston like member, and a method based on a micro pump or the like using a combination of micro actuator, diaphragm, check valve and the like, or a combination thereof may be used.

Examples of the micro pump are described in, for example, the aforesaid Proceedings of the μTAS '98 Workshop, held in Banff, Canada, 13-16 Oct. 1998. Editors: D. Jed Harrison and Albert van den Berg, Kluwer Academic Publishers and the like.

An example of feeding the liquid by means of pressure difference between the reservoir (vent) released to the outside and the reservoir (vent) pressurized with air pressure has been described above, but the liquid may also be fed by means of pressure difference between the reservoir (vent) decompressed with a pump and the reservoir (vent) released to the outside. In this case, the reservoir (vent) receiving the liquid is decompressed, and the reservoir (vent) sending the liquid is released to the outside. In addition, the liquid can be fed by means of pressure difference between the reservoir (vent) decompressed by the pump and the reservoir (vent) pressurized with air pressure. It is also possible to feed the liquid between reservoirs of different levels of pressurization, and between reservoirs of different levels of decompression.

(Detailed Description of Analyzing Cartridge)

The analyzing cartridge 1 of this embodiment comprises the plane member 100 provided on the surface with grooves through which the liquid is passed, and the cover sheet 130. And, the plane member 100 is bonded to the cover sheet 130 with the above described grooves therebetween, thereby forming the capillary 150 to prepare the analyzing cartridge 1.

This plane member 100 can be prepared with inorganic materials such as silicon and glass and organic polymers. In the case of silicon and glass, an etching protective membrane (Cr, etc.) is formed on a glass, quartz or Si substrate in the thickness of a few thousand angstroms using the process of vacuum evaporation or the like, and a patterning resist is coated thereon using a spinner. Thereafter, a mask for photolithography is used to expose the resist to ultraviolet light, followed by carrying out development (removing uncured portions with a solvent) to pattern the resist in a desired form.

Then, using the patterned resist as an etching mask, the etching protective membrane is dissolved away with a potassium ferricyanide solution or the like to pattern the same. Subsequently, using the patterned resist and etching protective membrane as masks, the substrate is etched with, for example, a fluoric solution to form grooves. Thereafter, the resist and protective membrane are etched away. Also, in addition to the above described substrate, a substrate of glass or the like in which through-holes are provided using the process such as super sonic machining is prepared. Finally, the substrate provided with grooves and the substrate provided with through-holes are bonded to each other with the grooved therebetween, and are heated in, for example, a vacuum oven (if both of the substrates are glass substrates, they are heated at 600° C. for a few hours), and are then left for cooling, whereby they can be fusion-bonded to prepare the plane member.

The plane member 100 can also be produced based on Method of Producing Circuit Board of Japanese Patent Laid-Open No. 6-283830. If the glass substrate is used in this method, a method is used in which a resist pattern is formed on the glass substrate, and the glass substrate is processed by the sand-blast process. Since flying particles are all made to move in the vertical direction due to the thick resist, it is possible to process the substrate sharply compared to a usual thin resist, and grooves of high aspect ratios can be formed. Also, a method can be used in which a photosensitive resist is coated on the glass or resin substrate to expose portions other than grooves to light, followed by removing uncured portions to form a groove-shaped resist pattern on the substrate.

In the case where the organic polymer is used to prepare the plane member 100, if optical detection is carried out, a resin transparent to the light with wavelengths to be used for detection should be used. For example, in the case where detection is carried out using a photothermal converting detection method, light transmittance of a resin measured with the method of ASTM D1003 is 80% or larger, preferably 90% or larger. Also, in the case of detection by spectrophotometry, chemiluminescence and fluorimetry, the transmittance is 80% or larger, preferably 90% or larger.

Furthermore, the wavelengths of exciting and detecting lasers capable of being used in each method are in the range of from 400 to 800 nm, preferably from 600 to 800 nm in the case of the photothermal converting detection method. And, generally, the wavelengths are in the range of from 500 to 800 nm in the case of detection by spectrophotometry if taking a $H_2O_2$-peroxytase system as an example, and in the range of from 400 to 600 nm in the case of detection by chemiluminescence, and in the range of from 480 to 700 nm in the case of detection by fluorimetry.

In addition, in the case where the photothermal converting detection method is used, the thermal lens is formed also in the resin due to minimal absorbance of resin to cause a background, and therefore the absorptance of light by resin is 5% or smaller, preferably 1% or smaller, further preferably 0.5% or smaller of excitation light and probe light in the total optical distance in the resin.

In addition, in selecting the material of an organic polymer for use in the plane member 100 having grooves, molding processability is one of important factors. Materials that can be used suitably in terms of molding processability include thermoplastic resins that can be subjected to usual melt processing and resins obtained by UV curing. Furthermore, the former is more suitable in a sense that the plane member 100 having grooves in its surface can be formed in a large quantity and inexpensively.

In particular, amorphous thermoplastic resins, thermoplastic polymer alloys having amorphous resin as a main component, or some crystalline thermoplastic resins having low crystallinity are suitable. Specifically, styrene based resins such as polystyrene and styrene-acrylonitrile copolymers, methacryl resins such as polymethyl methacrylate (PMMA) and methyl methacrylate-styrene copolymers, polycarbonate (PC), polysulfone (PS), polyethersulfone, polyetherimide, polyarylate, polymethylpentene and the like can be suitably used.

Also, 1,3-cyclohexadiene based polymers are suitably used. For the 1,3-cyclohexadiene based polymers, homopolymers can be used, but copolymers can also be used. These copolymers include copolymers with chain conjugated diene based-monomers such as 1,3-butadiene, isoprene, 1,3-pentadiene and 1,3-hexadiene, vinyl aromatic monomers such as styrene, α-methyl styrene, p-methyl styrene, 1,3-dimethylstyrene, vinyl naphthalene and vinyl styrene, polarized vinyl monomers such as methyl methacrylate, methyl acrylate, acrylonitrile, methyl vinyl ketone and methyl α-cyanoacrylate or polar monomers such as ethylene oxide, propylene oxide, cyclic lactone, cyclic lactam and cyclic siloxane, or ethylene, α-olefin based monomers. For copolymerization ratios, the ratio in weight of 1,3-cyclohexadiene monomer to comonomer is preferably in the range of 75/25 to 100/0.

Cyclohexadien based polymers of high light transmittance are described in detail in Japanese patent Application No. 9-277045 Specification. Because such polymers have little absorption at the wavelengths above 200 nm, and are amorphous C—H polymers, they can also be detected with a short-wave light source.

The plane member made of organic polymer having grooves on the surface can be produced by UV curing or heat curing of monomers and macromonomers in molds, melt processing and plasticity processing of thermoplastic resin, machining of the plane member having no grooves on the surface or etching thereof by the laser or the like, and so on. Forming methods that can be used suitably include melt processing and plasticity processing of thermoplastic resin in a sense that plane members having grooves on the surface can be produced in a large quantity and inexpensively. Processes that can be used further suitably include injection molding and/or compression molding using molds and emboss forming process of thermoplastic resin.

In particular, an injection molding method in which injection molding is carried out while reducing the solidification temperature of the resin surface contacted with the mold during process of loading resin into the mold cavity (Japanese Patent Laid-Open No. 10-128783A, Japanese Patent Application No. 10-46665 specification and Japanese Patent Application No. 10-50719 specification) can be especially a preferable method because the method enables plane members made of organic polymer having highly accurate and fine grooves to be produced in good producibility. Specific examples of this injection molding method include a method in which the cavity is filled with carbon dioxide gas before injection molding is carried out. The pressure of the carbon dioxide gas in this case is preferably 10 MPa or smaller.

In addition, injection molding methods in which the surface of the mold is heated to carry out molding, such as an injection molding method in which the surface of the mold is heated by high-frequency induction heating immediately before molding is carried out (described in Japanese Patent Publication No. 62-58287B, U.S. Pat. No. 4,439,492 specification and the like), and a method in which the surface of the mold is heated by radiation heating immediately before molding is carried out (described in Molding Symposia '95, 241<1995>, Molding '96, 69<1996>, Synthetic Resin, 42 vol. (1), 48 <1992> and the like) are also preferable methods.

In other words, the above described molding methods are preferable because they enable compatibility between the mold surface transferability and the molding cycle to be achieved by heating selectively the surface of the mold with heat sources such as high-frequency induction heating and halogen lamps immediately before molding is carried out.

For molds for forming the plane members, molds composed of metals that are generally used for molding of synthetic resin, such as iron or steel materials having iron as a main component, aluminum or alloys having aluminum as a main component, zinc alloys and beryllium-copper alloys can be used suitably.

One example of methods for producing a mold will be described. First, a matrix having the surface form of a desired plane member having fine grooves is prepared from a material such as metal, plastic, silicon or glass using a method such as machining, etching, or photolithography processing of ultraviolet-cured resin. And, the mold is produced from this matrix by an electrochemical molding method using nickel or the like.

In addition, the mold can also be produced using the above described method of Japanese Patent Laid-Open No. 6-283830 in which the resist patter is formed. After the resist pattern is formed on a metal substrate, portions in which no resists exist are filled with plated metal. Then, the resist is removed to form a metal plate with a fine pattern provided on the surface. Resin and sintered glass can be processed using this metal plate as a mold.

Also, the analyzing cartridge comprising a plane member made of organic polymer having grooves may have the inner surfaces of the grooves subjected to protein adsorption prevention processing by means of graft polymerization of polyethylene glycol. Also, in the case where electroosmotic flows described later are used as means for feeding the liquid, surface treatment may be carried out for producing stable electroosmotic flows.

The analyzing cartridge 1 of this embodiment is formed by bonding the plane member 100 and the cover sheet 130 together with the above described grooves therebetween by ultrasonic seal, heat seal, bonding with a hot melt adhesive and UV adhesive, sticking with a tackiness agent, bonding with a double faced adhesive tape, and direct pressure welding or pressure welding via a thin elastic sheet.

The material of the cover sheet 130 may be selected from the materials for use in the plane member 100, and same or different materials may be used. The thickness thereof is not particularly limited unless optical detection is adversely influenced, but it is preferably in the range of from about 0.05 to a few mm.

Also, the analyzing cartridge 1 of this embodiment may be preferably a structure in which the plane member 100 having grooves on the surface is bonded to the cover sheet 130 with the above described grooves therebetween, in terms of producibility, but it may be a three-layer structure in which a plane member having through-holes may be placed between two cover sheets to form grooves.

This cover sheet may be provided with through-holes for reservoirs, or may be provided with cylindrical or rectangular reservoirs (including waste liquid storing reservoirs) in such a manner as to protrude from the plane member 100. The sizes of the protruding reservoirs should not be particularly limited, but it is preferable that the height is approximately in the range of from one to a few mm and the diameter is in the range of from one to a few mm. If the plane member having grooves and the cover sheet has the thickness of a few mm, the above described through-hole can also have a role as a reservoir.

In this embodiment, the shapes of the cross sections of the grooves provided on the plane member 100 may be the shapes of polygons such as rectangles and triangles, semi-circles and semi-ellipse without being particularly limited. Also, the plane member 100 may have on the surface channels formed by combining together some grooves of different shapes. The width of the upper face (opening portion) of the groove may be identical to or larger than that of the lower face (bottom) Furthermore, most preferably, the cross-section of the groove has a rectangular cross-section shape.

Clogging may be caused by fine particles entrained in the liquid or by blood cells if this groove is too small. Also, the efficiency of mixing by diffusion when two liquids are merged and mixed is reduced if the groove is too large. Therefore, it is preferable that the width of the groove is in the range of from 1 to 500 µm, the depth thereof is in the range of from 0.1 to 1000 µm, and the area of cross section is in the range of from 1 to 250000 µm². More preferably, the width of the groove is in the range of from 2 to 300 µm, the depth thereof is in the range of from 1 to 200 µm, and the area of cross section is in the range of from 2 to 60000 µm².

The dimensional accuracy of the grooves provided on the surface of the plane member 100 is not particularly defined. However, when analysis of a very small amount of component or quantitative analysis is carried out, a high degree of dimensional accuracy is preferred. That is, for ensuring accuracy of operations and reproducibility among individual analyzing cartridges, the dimensional accuracy of the groove is preferably within ±5% of the design dimension for the width and depth, and within ±7% of the design dimension for the sectional area. Also, it is further preferable that the dimensional accuracy is within ±2% for the width and depth and within ±4% for the sectional area for highly accurate quantitative analysis.

In the case where the quantitative reaction in the analyzing cartridge 1 of this embodiment is carried out in such a way that by controlling the ratio of flow rates, liquids are mixed at a fixed ratio to carry out reaction continuously for at least a certain time period (Japanese Patent Application No. 10-181586 Specification by the inventor, "Mixing Analysis Apparatus and Mixing Analysis Method"), the analyzing cartridge 1 is formed by the plane member 100 having grooves, and has individual channels for a sample and for at least one type of reagent solution, channels linking to channels provided with detection portions after those channels are merged one after another or at a time, and a mechanism for controlling flow rates. Furthermore, the flow rate refers to the volume of the liquid moving in the groove (capillary) in a predetermined time period.

(Description of Vent)

For the vent 141 for use in this embodiment, any material may be used as long as it is a material through which the liquid in the analyzing cartridge 1 cannot be passed but a gas, particularly air can be passed.

If the liquid in the analyzing cartridge 1 is a solution, a hydrophobic material provided with holes may be used. If the hydrophobic holes are used as the vent, only a gas is passed through the vent because the solution is not passed therethrough because of its surface tension, thus reducing possibilities that the liquid is leaked out compared to materials that do not have hydrophobiities.

One of preferred embodiments of the vent is a plane plate, sheet or the like composed of a hydrophobic polymer or inorganic material provided with a small number of small holes having diameters of about 1 μm to a few hundred μm. Even though the vent of one reservoir is provided with only one to a few holes, a sufficient function as a vent can be added if the size of the holes and the hydrophobicity of the material is appropriately selected. These holes may be bore mechanically with a drill or the like, or may be bore using a laser or the like.

Preferably, the hydrophobic organic polymer has a critical surface tension of about $4 \times 10^{-2}$ N/m or smaller at 20° C., examples of the polymer including polytetrafluoroethylene (PTFE), silicone, siloxanes, polyethylene, polypropylene, polystyrene, polyvinyl chloride, polycarbonate, polysulfone, polyethersulphone, polyarylate, polymethylpentene and 1,3-cyclohexadiene based polymers.

On the other hand, in the case where the liquid in the analyzing cartridge 1 is a hydrophobic organic solvent, a hydrophilic porous membrane is suitably used. Furthermore, a plane plate, sheet, membrane or the like composed of a hydrophilic material, which is provided with small holes as in the case of solutions, can also be used as the vent.

For analysis in medical diagnosis, the liquid in the analyzing cartridge 1 often has water as a main component, and therefore a hydrophobic material is used for the vent.

For the vent, not only a material provided with a small number of holes of small diameters but also a porous membrane may be used. In production of the analyzing cartridge, producibility is enhanced because the vent can be formed simply by bonding a hydrophobic porous membrane to a formed chip. Also, the liquid in the reservoir can be pushed out into the capillary by pressing this hydrophobic porous membrane to apply pressure, which is preferable.

For the hydrophobic membrane material, the above described hydrophobic organic polymer is suitably used. However, in biochemical analysis of GOT/GPT, cholesterol levels and the like, a surfactant is often added to the reagent generally for the purpose of preventing absorption of plasma proteins and so on, and therefore a more hydrophobic membrane needs to be used in this case.

Usually, there are cases where a cellulose acetate membrane may be used, but when a reagent with a surfactant added therein is used, a membrane of high hydrophobicity such as PTFE, silicone and polyethylene is more preferable because such a membrane has a strong capability (anti-water pressure) to prevent the liquid from being leaked from the vent. If the process where a non-fluid reagent is dried and fixed on the vent is taken into consideration, the PTFE membrane more stable in shape to the reagent containing a surfactant or the like has the high hydrophobicity, and thus is preferable.

Since the liquid can be fed at high pressure, the higher the anti-water pressure of the vent, the more preferable, and the anti-water pressure of the vent is preferably 100 g/cm$^2$ or higher, more preferably 1000 g/cm$^2$ or higher, and further more preferably 3000 g/cm$^2$ or higher.

In the case where this hydrophobic porous membrane is used as the vent in the reagent storing reservoir and the like, if the fluid pressure is too high when the reagent dissolving liquid is fed to the reagent storing reservoir, the hydrophobic porous membrane may be expanded to introduce a large amount of reagent dissolving liquid to reduce the concentration of the reagent solution. Therefore, the hydrophobic porous membrane with the surface (opposite to the reagent storing reservoir) reinforced with a non-woven fabric such as polypropylene is used as one of preferred embodiments.

Methods in which a sheet having holes or a hydrophobic porous membrane is bonded to a chip provided with through-holes to form a vent include a method in which they are bonded together using a heat curing or UV curing adhesive, a double-faced adhesive tape or the like.

It is problematic if the adhesive or double-faced adhesive tape exists in a portion having a function as a vent in the sheet having holes or the hydrophobic porous membrane, namely the portion covering the through-hole. Thus, a pretreatment is needed such that the portion covering the through-hole is masked if the adhesive is coated, or a portion corresponding to the portion covering the through-hole is punched to provide a hole therein in advance if the double-faced adhesive tape is used. In the case of the double-faced adhesive tape, a method in which a mold having a blade for punching the portion covering the through-hole is prepared in advance, and the sheet having holes or the hydrophobic porous membrane is continuously bonded to the chip provided with through-holes while the double-faced adhesive tape is punched is preferable in terms of efficiency of production.

The direction in which a gas is passed in the hydrophobic porous membrane is usually a direction perpendicular to the surface of the hydrophobic porous membrane, namely the direction of thickness. However, the gas can also be passed in the direction parallel to the surface of the hydrophobic porous membrane (hereinafter described as lateral direction) That is, it is also possible to cover the face opposite to the reservoir of the hydrophobic porous membrane with a non-gas permeable material such as a PET membrane to prevent the gas from being passed in the direction of thickness, thereby passing the gas in the lateral direction from the reservoir to the end of the membrane. Generally, however, passing the gas in the direction of thickness is more preferable in a sense that the structure of the vent can be simplified.

In addition, there are cases where passing the gas in the lateral direction of the membrane has an undesired influence on the control of the feeding of the liquid in the analyzing cartridge. If each reservoir is individually provided with the hydrophobic porous membrane, namely if the hydrophobic porous membrane covering only the openings of one reservoir is provided, there arises no problem. However, if the openings of a plurality of reservoirs are covered with one hydrophobic porous membrane, a problem may arise.

That is, there arises no problem when the access of the liquid to a plurality of reservoirs is controlled in the same way (with the same pattern), but when the access of the liquid to each reservoir is to be controlled independently, if the gas is passed in the lateral direction, then the gas may be leaked into the vents of adjacent reservoirs to cause a hindrance to accurate control. Thus, for controlling the access of the liquid to a plurality of reservoirs when one hydrophobic porous membrane is used as a vent for a plurality of reservoirs, the gas should be prevented from being passed in the lateral direction of the hydrophobic porous membrane.

For this purpose, it is preferable that the openings of each reservoir are covered with an individual hydrophobic porous membrane, but when the openings of a plurality of reservoirs are covered with one (common) hydrophobic porous membrane (it is more preferable that they are covered with one hydrophobic porous membrane, in terms of producibility for the analyzing cartridge), the portion of the hydrophobic porous membrane located between reservoirs needs to be impervious to the gas.

Thereby, a situation in which the gas is passed in the lateral direction to have an adverse influence on the control of the access of the liquid to the adjacent reservoirs is eliminated. For making the hydrophobic porous membrane impervious to the gas, it is necessary to fill up the holes provided in the hydrophobic porous membrane to eliminate holes, namely deprive the membrane of porosity.

For methods for achieving this purpose, specifically, a method in which the portion located between reservoirs is impregnated with an adhesive or solvent, a method in which the portion is melted by heating, a method in which pressure is applied to the portion and the like can be considered. For the method in which the portion is melted by heating, however, the hydrophobic porous membrane may be crinkled, thus making it difficult to bond the membrane to the chip. The method in which the holes provided in the hydrophobic porous membrane are filled up by applying pressure thereto to eliminate holes is the most preferable of the above described methods. For preferable conditions for applying pressure, the temperature is kept at the normal room temperature, and the applied pressure depends on the thickness of the hydrophobic porous membrane and the average diameter of the holes.

Furthermore, also in the case of the reservoir group consisting of a plurality of reservoirs in which the control of the entry/exit of the liquid is carried out at a time, an independent hydrophobic porous membrane should be provided for each reservoir group, or if a plurality of reservoir groups are covered with a common hydrophobic porous membrane to form a vent for each reservoir, the above described hydrophobic porous membrane should have the portion between reservoir groups deprived of porosity. Thereby, the access of the liquid to each reservoir group can be controlled independently.

The average diameter of the holes provided in the hydrophobic porous membrane may be in the range of from 10 µm to 0.01 µm. However, considering the fact that the anti-water pressure is increased and the amount of air being passed per hour is reduced (i.e. the pressure and time required for passing the gas is increased) as the diameter of the hole is decreased, and with ease of acquirement taken into consideration, the average diameter of the holes is preferably in the range of from 0.05 to 5 µm. When the gas is passed in the direction of thickness of the hydrophobic porous membrane, the average diameter of the holes is preferably in the range of from 0.1 to 0.3 µm in terms of hydrophobicity or the liquid-barrier property and gas permeability. When the gas is passed in the lateral direction, the average diameter of the holes is preferably in the range of from 0.5 to 5 µm depending on the distance thereof.

Also, the thickness of the hydrophobic porous membrane is often in the range of from 20 to 300 µm, but it is preferably in the range of from 50 to 100 µm in terms of strength and the velocity at which the gas is passed.

(Description of Encapsulation and Dissolution of Non-Fluid Reagent)

One of the characteristics of the present invention is such that the non-fluid reagent is encapsulated in the reservoir provided with the hydrophobic vent as described above, and the above described reagent is dissolved to prepare a very small amount of reagent solution instantly in the analyzing cartridge at the time of analyzing a sample. This will be described in detail below.

In the analyzing cartridge of the present invention, at least some of the reagents to be encapsulated are non-fluid reagents. The above described reagents may be solid reagents such as powders, crystals and freeze-dried products, or may be rubber-like or glutinous starch syrup-like reagents as long as the above described reagent is not flown out into the capillary connected for communication with the reservoir during distribution of the analyzing cartridge (during transportation and storage) or at the time when the cartridge is handled.

The analyzing cartridge is distributed with this non-fluid reagent encapsulated in the reagent reservoir provided with the above described hydrophobic vent, and the reagent dissolving liquid encapsulated in or annexed to the analyzing cartridge is fed to the above described reagent reservoir through the capillary to dissolve the reagent immediately before the analysis is carried out.

Such a mechanism allows a very small amount of reagent solution, namely a few µl of reagent solution to be prepared in the analyzing cartridge without spending the reagent wastefully.

Also, because an analyzing cartridge with reagents encapsulated therein can be used as a product, the analysis operator can conduct desired analysis without carrying out operations for encapsulating the reagent in the analyzing cartridge if an analyzing cartridge with desired reagents encapsulated therein is purchased.

Methods for encapsulating the non-fluid reagent in the analyzing cartridge include a method in which a solid reagent, for example, a powdered or crystal reagent or a block of freeze-dried reagent is stored in a required amount in the reservoir, and a method in which a solution reagent is distributed into the reagent reservoir, followed by drying the same to give non-fluidity.

Figure 7:
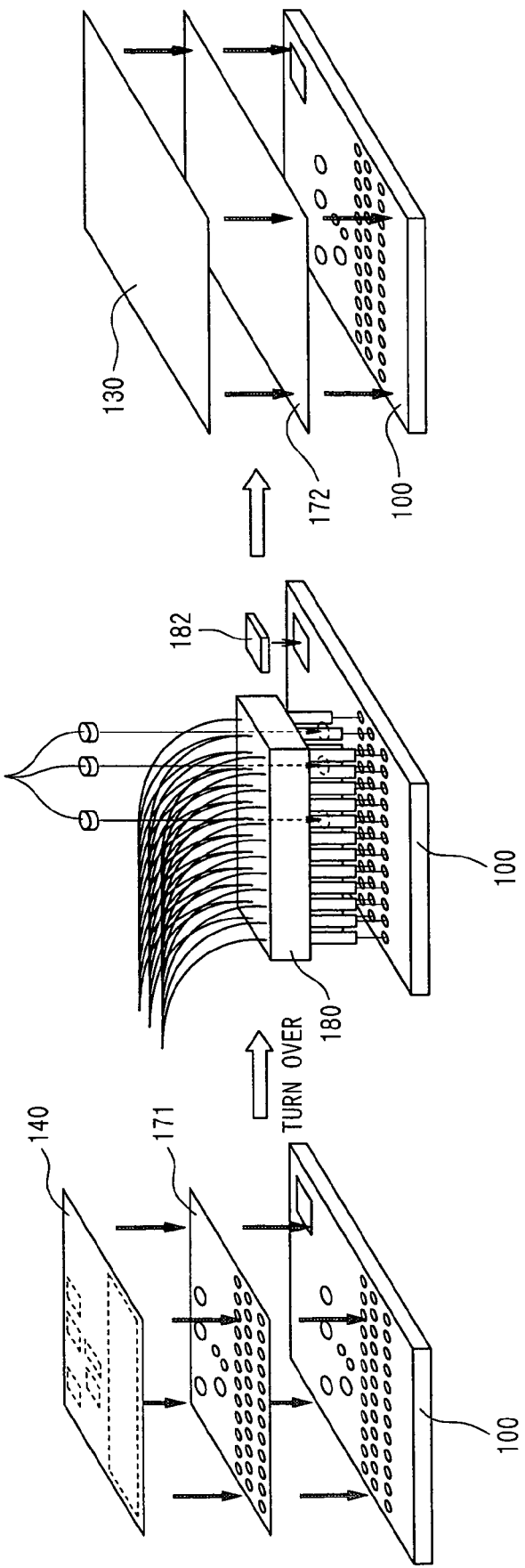
FIG. 7 is a conceptual view illustrating a process for producing the analyzing cartridge.

When the solution reagent is distributed, a venting membrane 140 made of ethylene tetrafluoride resin is bonded to the non-groove bearing face of the plane member 100 having through-holes with a double-faced adhesive sheet 171, and the reagent solution is introduced into the reservoir formed thereby with a distribution device 180 as shown in FIG. 7. Then, the reagent solution is dried into a non-fluid reagent, and thereafter the cover sheet 130 made of acryl resin having no pores is bonded to the face opposite to the above described face with a double-faced adhesive sheet 172, whereby the analyzing cartridge 1 of the present invention can be obtained.

Furthermore, the analyzing cartridge 1 is equipped with a portion pack 181 containing therein a standard solution, sample dissolving liquid and the like, and a filter 182 for separating blood cells from the total blood sample. Also, in the venting membrane 140, the gas is prevented from being passed in the lateral direction by applying pressure to the portion surrounding the openings of the above described reservoir. In addition, in the double-faced adhesive sheet 171, the portion corresponding to the portion covering the openings of the above described reservoir is punched in advance to provide holes.

Due to recent advancement in DNA chips, the technique in which volumes ranging from a very small amount in the order of 1 nl to the order of microliters are measured in a few % or smaller as a CV value is established, and therefore the reagent can be measured accurately and encapsulated in the analyzing cartridge 1 if a dot plotter of such technique (e.g. Pixsys 3000 manufactured by BioDot Co., Ltd.) is used as an injection device for injecting a reagent solution.

In addition, even if the venting membrane 140 is bonded to the cover sheet 130 in the order reverse to the aforesaid order, the analyzing cartridge 1 can be prepared. That is, the cover sheet 130 is bonded to the groove bearing face of the plane member 100 having through-holes with a double-faced adhesive sheet 172, and the reagent solution is introduced into the reservoir formed thereby. Then, the reagent solution is dried into a non-fluid reagent, and thereafter the venting membrane 140 made of ethylene tetrafluoride resin is bonded to the face opposite to the above described face with the double-faced adhesive sheet 171, whereby the analyzing cartridge 1 of the present invention can be obtained. Furthermore, in this case, a reagent solution of high viscosity (low fluidity) is preferably used to make it difficult for the reagent solution to flow into the capillary.

This will be described using FIGS. 1 and 2. The solution reagent is deposited in the reservoir or on the vent 141 covering the reservoir in a dotted form using an apparatus such as a dot plotter. Then, the solution reagent is dried, followed by bonding the cover sheet 130 to the plane member to encapsulate the non-fluid reagent 160 in the analyzing cartridge 1. Alternatively, a method may be used in which before bonding the sheet to the plane member 100 provided with grooves, the solution reagent is deposited in a dotted form in the position opposite to the reservoir of the venting membrane 140 to be dried, followed by bonding the venting membrane 140 and the cover sheet 130 to the plane member 100.

In this case, however, positioning accuracy when the reagent solution is deposited needs to be ensured as a matter of course, but the post-drying diameter of the reagent deposited in a dotted form also needs to be controlled. In other words, the post-drying diameter of the deposited reagent is reduced so that it is smaller than the diameter of the reservoir as a matter of course, but also, the air should easily be purged when the reagent dissolving liquid for dissolving the reagent is injected. To this end, the post-drying diameter of the deposited reagent is slightly smaller than the diameter of the reservoir, preferably 90% or less of the diameter of the reservoir.

The reagent solution injected into the reservoir can be dried naturally even at the normal room temperature and under the normal atmospheric pressure in the circumstance where humidity is kept at a low level, because its amount is very low. In terms of production efficiency, it is desirable that the reagent is dried in a short time under a reduced pressure such as a pressure below the atmospheric pressure. In that case, the reagent is preferably dried based on a vacuum program that prevents bumping and the like. Freeze-drying can also be used, but may cause the plane member to be deformed and deteriorated. Furthermore, the reagent may be a semi-dried substance or a pasty substance resulting from addition of a hydrous polymer and polysaccharide as long as the reagent does not flow even if the analyzing cartridge 1 is tilted.

Also, the reagent solution may be freeze-dried separately and stored in the reservoir provided with the hydrophobic vent, followed by sticking the cover sheet thereto to cover the reservoir. If the reagent solution in the amount equal to or smaller than the amount of reagent solution to be encapsulated in the reservoir is deposited on an appropriate sheet or the like in a dotted form, and is freeze-dried, the reagent can easily be stored in the reservoir. It is also possible to produce small reagent particles when a reagent solution is dropped in liquid nitrogen through a nozzle with an appropriate diameter.

In addition, the non-fluid reagent is formed into tablets outside the analyzing cartridge, and the tablets are encapsulated in the reservoir. However, the above described method using a solution reagent is more preferable in terms of producibility.

On the other hand, for reducing a dissolving time period over which the non-fluid reagent encapsulated in the analyzing cartridge is dissolved in the reagent dissolving liquid just before analysis, a dissolving adjuvant can be added in the non-fluid reagent for some measurement items. For the dissolving adjuvant, polyether such as polyethylene glycol (PEG) having an appropriate molecular weight distribution, a monosaccharide such as glucose, a disacchride such as shoecrose, a polysaccharide such as dextran and pluran, an oligosaccharide or a mixture thereof is used.

Of the above dissolving adjuvant, at least one type of adjuvant selected from polyols, particularly ethylene glycol, propylene glycol and glycerol is preferable. As shown in Experimental Example 2 described later, the polyol was effective even when addition of PEG often used as a dissolving adjuvant in the past was not effective. And, of polyols, preferable is glycerol, which had a significant adjuvant effect on a reagent for which only a small effect was brought about by addition of polyethylene glycol.

(Description of Samples)

In environmental analyses, river water, sea water and waste water from the factory can be used as samples. Also, in medical diagnosis examination, blood and the like can be used as samples. The blood can be used as sample in any form such as plasma, blood serum and total blood. When the sample is in the form of plasma or serum, losses involved in separation of blood cells are prevented, and therefore the amount of sample actually required for analysis can be very small, namely 1 µl or smaller.

In general, the blood cell should be removed from total blood to provide plasma when biochemical examination is carried out. Thus, in the case where total blood is directly introduced into the analyzing cartridge 1, a few ten µl is preferable as an amount of sample. For methods for obtaining the plasma from the total blood, there is a method in which the analyzing cartridge 1 is treated with a centrifugal separator to carry out centrifugal separation in the analyzing cartridge 1, but a method in which the total blood is passed through a plasma separating filtration membrane to separate the plasma is preferable in terms of convenience. Plasma separating filtration membranes include cellulose filters, Teflon filters and glass filters. Of these, the glass filter (e.g. GF-D manufactured by Whatman Co., Ltd.) is preferable in terms of plasma recovery.

On the other hand, when measurements of leucocyte number, erythrocyte number, palatelet number and the like are carried out in the analyzing cartridge 1, because the total blood sample is directly diluted and hemolyzed to be used, a plasma separating membrane as described above is not necessary, and the amount of total blood may be very small, namely 1 µl or so.

(Description of Reagent Dissolving Liquid and Sample Diluent)

The reagent dissolving liquid and the sample diluent are liquid reagents that are required in the amount of a few ten µl or larger in analysis, and thus can be encapsulated in a bag such as the aforesaid portion pack and placed in the analyzing cartridge 1. The material of the bag is not particularly limited as long as the bag is not degraded, and can easily be opened to let the contents leak into the capillary and reservoir of the analyzing cartridge 1. A bag composed of an organic polymer, a bag composed of an organic polymer deposited with aluminum, a bag having a structure of multiple layers and the like are preferable in terms of stability of reagents.

The method for opening the above described bag may be a method in which the bag is broken with a raised object as shown in FIG. 3, or a method in which the portion corresponding to the lid is pushed or pulled to remove the portion from the bag body, thereby opening the bag. Furthermore, a mechanism for opening the above described bag may be provided in the analysis apparatus, or the analysis operator may carry out opening operations just before use.

(Description of Vent for Feeding Liquid Using Centrifugal Force)

The form in which the vent is provided on one face of the analyzing cartridge 1 has been described, but when the feeding of the liquid is carried out using centrifugal force (centrifugal liquid feeding), the vent may be provided on one or both of the upper and lower faces of a disk cartridge. In this case, since there may be cases where the vent hinders optical detection, the vent may be provided on the outer face of the disk cartridge, namely in the direction of centrifugal force. Because only one reagent reaction can be carried out if reservoirs are provided along the outer face of the disk cartridge, a method can also be adopted in which a plurality of reagent storing reservoirs are provided inside the disk cartridge, and the outlet of each reservoir is opened with a wax valve (valve that is opened by melting wax) and a valve that is opened by breaking a balance between centrifugal force and surface tension to let the reagent solution flow out into the reaction channel.

(Description of Liquid Feed Control Device)

The liquid feed control device is not particularly limited as long as the device is configured to be capable of allowing or regulating the entry/exit of the gas via the vent 141.

A typical example thereof is a liquid feed control device comprising a valve for controlling the allowing or regulating of the entry/exit of the gas via the vent 141, a pump that is coupled to the above described valve and is capable of supplying and suctioning the gas, a coupler for coupling the above described valve in the position opposite to the reservoir with the vent 141 therebetween, and a tube connected for communication between the above described valve, and the above described pump and the above described coupler.

The coupler needs to be adhered to the analyzing cartridge 1 so that airtightness is maintained. To this end, the surface contacting the analyzing cartridge 1 should be provided with packing composed of a material that is generally used for an O-ring, or the coupler itself should be composed of such a material having good adhesiveness and airtightness. Also, packing composed of a material such as an O-ring may be provided on the analyzing cartridge 1 side.

Such a material is generally a synthetic rubber material. For example, the material is ethylene propylene rubber, silicone rubber, nitrile rubber, chloroprene rubber, isoprene rubber, butadiene rubber, styrene butadiene rubber, butyl rubber, ethylene propylene rubber, urethane rubber or the like.

Also, the portion of the coupler contacting the analyzing cartridge 1 may be shaped into a sharp knife-edged portion to couple the coupler to the analyzing cartridge in such a manner that the knife-edged portion is stuck into the analyzing cartridge 1. In this way, sufficient airtightness can be ensured. Furthermore, in contrast to the above method, the portion of the analyzing cartridge 1 contacting the coupler may be shaped into a sharp knife-edged portion to couple the analyzing cartridge 1 to the coupler in such a manner that the knife-edged portion is stuck into the coupler.

Figure 8:
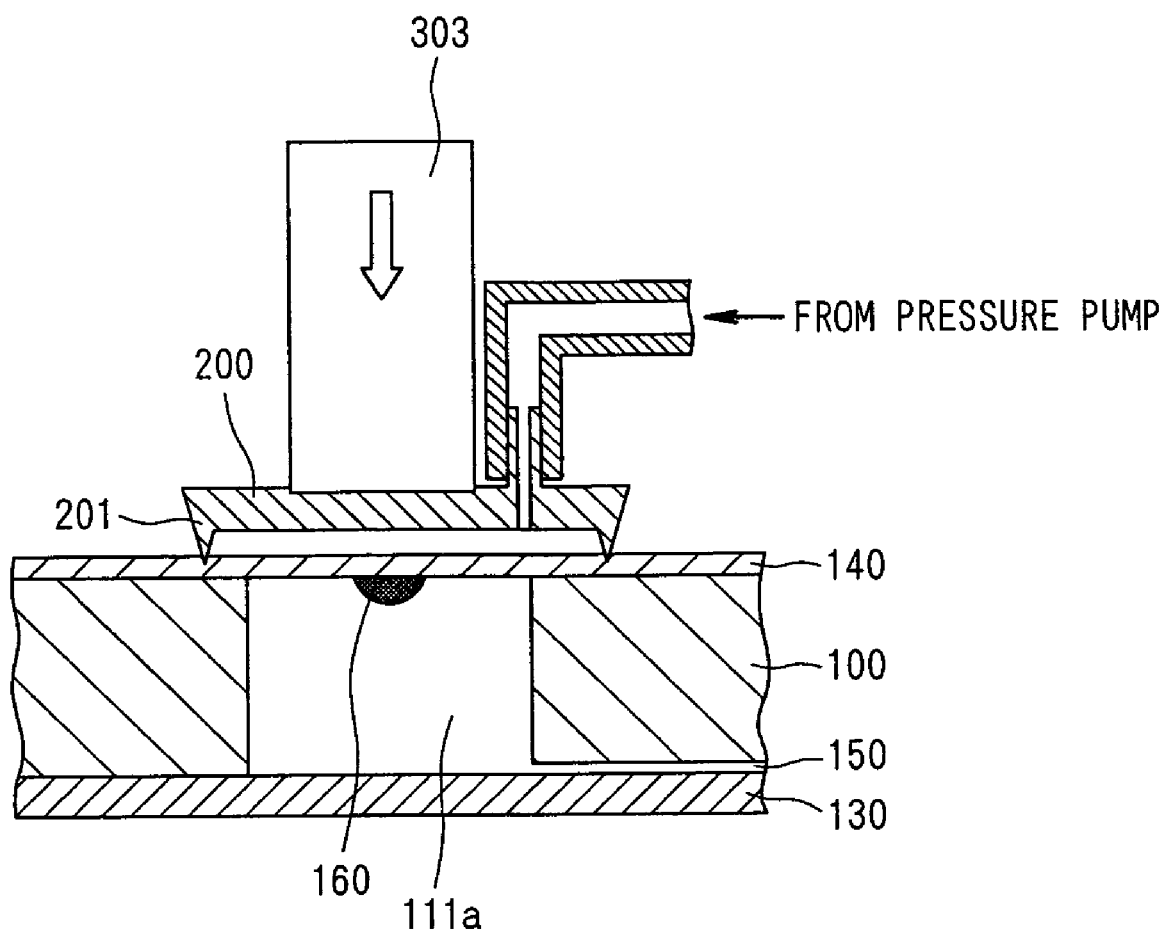
FIG. 8 is a sectional view illustrating a structure of a coupler in which the portion contacting the analyzing cartridge is like a knife-edge.

An example in which the portion of the coupler contacting the analyzing cartridge 1 is shaped into a sharp knife-edged portion to couple the coupler to the analyzing cartridge in such a manner that the knife-edged portion is stuck into the analyzing cartridge 1 is shown in FIG. 8.

The knife-edged portion 201 is provided along the outer region of the circular or rectangular coupler 200. And, the coupler 200 is pressed against the analyzing cartridge 1 with a piston 303 similar to the piston used for pressing the aforesaid portion pack to stick the knife-edged portion 201 into the analyzing cartridge 1, whereby the coupler 200 and the analyzing cartridge 1 are coupled together. In this way, the coupler 200 can be coupled to the analyzing cartridge 1 with sufficient airtightness maintained.

Furthermore, if a plurality of reservoirs are covered with one hydrophobic porous membrane to form the vent, the holes of the hydrophobic porous membrane are filled up as a result of pressing the above described knife-edged portion, and thus the portion located between reservoirs is deprived of porosity. Consequently, the gas can be prevented from being passed through the hydrophobic porous membrane in the lateral direction.

Also, the pump to be used is not particularly limited as long as it can produce a required level of pressure. Generally, pressure-type pumps are often used, but vacuum-type pumps may also be used as described above.

Furthermore, if quantifiability is required, a micro syringe pump, a small flow peristaltic pump, a linear pump based on a micro actuator or the like is used.

In addition, a bimetal and piezoactuator are also used as a driving force production source, and gravity and centrifugal force can be used as liquid feed driving force.

(Description of Electric Feeding Method)

A part of the feeding of the liquid based on the pressure difference of the gas as described above may also be carried out by an electric feeding method using electrophoresis, electroosmotic flows or the like in which an electric field is applied to the liquid in the capillary (described in detail in "Capillary Electrophoresis", Kodansha, etc.). The method using electroosomosis flows is a method in which the liquid in the capillary is moved in association with the movement of ions on the inner surface of the capillary, and if the capillary is formed by glass and silicone, protons of silica on the glass and the like surface provides movement force.

Also, even if the plane member 100 composed of an organic polymer such as PMMA, polycarbonate resin (PC) or the like is used, and no particular ion species exist on the inner surface of the capillary, the electrolyte in a liquid may be absorbed onto the inner surface of the capillary to produce electroosomosis flows by means of its electric charge, depending on the composition of a liquid flown through the capillary. For producing stable electroosomosis flows, an organic polymer having a sulfonic acid group or carboxyl group may be added to the inner surface of the capillary by graft polymerization or the like. In the case of the organic polymer having carboxylate group such as PMMA, it is preferable that the surface of the groove is partially hydrolyzed with a sodium hydroxode solution or the like to expose a carboxyl group for stabilizing the electroosmotic flow.

Adoption of the electroosomosis flow constitutes one of preferred embodiments because for the electroosomosis flow, the flow rate can correctly be controlled through control of voltages, finely and quickly, and in accordance with a set program, thus making it possible to control accurately the reaction and separation in the analyzing cartridge 1.

For the power supply for producing the electroosomosis flow, a high-voltage power supply device (e.g. Mode 1 HCZE-30PNO, 25, Matsusada Precision, voltages up to 30 kV can be applied) is used, and this can be controlled from an external computer via an interface board (e.g. DAQCard-1200, CB-50 Connector Block, manufactured by National Instrument Co., Ltd.). A program for voltage application timing and the like may be produced with, for example, NI-DAQ Drive Software (LabVIEW) and the like.

For producing the electrophoresis and electroosmotic flow to feed the liquid, metal needle electrodes, electrodes printed with conductive ink or metal eyelet inserted electrodes needs to be provided in such a manner that the electrodes contact the groove portion and the cover sheet 130, or contact reservoirs (for storing reagents, samples, buffers, waste liquids and the like) located at the ends or some midpoints of grooves.

In the case where the metal needle is inserted, a needle made of platinum, copper or the like that is 0.1 to 1 mm in diameter and is long enough to reach near the groove of the plane member 100 is fixed in the inlet and outlet hole using an appropriate supporter or the like.

In the electrode printed with conductive ink, the ink containing fine particles of gold, copper, nickel, carbon black, graphite or the like is printed or deposited on the entire surface or a part of the surface of the inner wall of the above described hole to the depth reaching near the groove of the plane member 100. Also, in the case of vacuum deposition and spatter coating, similarly gold or platinum are printed or deposited on the entire surface or a part of the surface of the inner wall of the above described hole to the depth reaching near the groove of the plane member 100. At this time, if the above described hole is tapered, the electrode can be formed in the inner wall without tilting the plane member 100.

In the case of the metal eyelet (cylinder with rib), an electrode having a diameter such that it adheres to the inner wall of the through-hole and a length such that it reaches near the groove of the plane member 100 is used. The material thereof is not particularly limited, but for preventing a reaction on the electrode, platinum-plated brass, copper, nickel and the like are preferable. The "rib" of the above described eyelet has an effect of enhancing conductivity between the above described eyelet and the wire on the plane member 100.

Also, in addition to the above described electrodes, electrodes for connection with the electric power terminal in the analysis apparatus with the analyzing cartridge 1 mounted therein, and leads between those electrodes may be formed with conductive ink, vacuum evaporation coating and spatter coating. Also, they may be formed by attaching a thin plate such as a copper plate, and then forming a wiring pattern with etching, and by transferring or attaching a patterned copper foil or the like onto the plane member 100. In any case, the material and size should be selected so that heat generation occurring when high voltage is applied can be reduced so as not to have an influence on electrophoresis.

(Description of Flow Rate)

For the form of a channel portion mainly intended for the mixing and dilution of the sample and reagent, a form in which a channel joins another channel, and a form in which a channel joins a plurality of channels at one point are adopted. By joining a channel with another channel or a plurality of channels into one channel, mixing operations and dilution operations can be carried out.

In addition, at this time, by the flow rate in each channel, mixing and dilution can be carried out at different ratios. For the ratio at which the mixing and dilution are carried out, the flow rate in each joining channel can be changed mechanically in the case of feeding of the liquid by a pump, and the flow rate in each joining channel can be changed by changing the size of the section and the length of each joining channel, by changing the process of applying voltage to each channel, and changing charged conditions of the inner surface of each joining channel capillary by surface treatment in the case of feeding the liquid with the electroosomosis flow. In the case of feeding the liquid by pneumatic pressure, it is preferable that a difference in pressure applied to each reservoir, viscosity of the liquid and the like are considered, and pressure losses in association with the sectional area and length of the channel are determined to design the channel.

If detection can be carried out without involving separation of the sample from the reagent after reaction as in the case of biochemical examination items, operations from mixing to reaction to detection can be continuously conducted with consistent channels without measuring fixed amounts of sample and reagent for separation. Generally, if a component to be detected can be detected without being hindered by other contaminants in relation to, for example, absorption wavelengths, or if the substance to be detected is changed as in the case where the hydroxyl group in the sample is oxidized, and the resulting carbonyl group is detected with a spectrophotometer, operations from mixing at a predetermined ratio of flow rates to reaction to detection can be conducted with consistent channels without performing separation operation.

In a method like this in which the mixing ratio is defined by ratio of flow rates to carry out a reaction, it is not necessary to conduct mixing and reaction continuously for a longtime. For example, if mixing requires 10 seconds, minimum 10 seconds (usually, slightly longer: about 20 seconds) are spent to merge the sample and the reagent, the mixture of sample and reagent is moved through the groove for a time long enough to complete a reaction, and thereafter minimum ten seconds are spent to merge the mixture and another reagent. Then, the resulting mixture is moved through the groove for a time long enough to complete a reaction, followed by conducting detection.

(Description of Detection Method)

If the total cholesterol, triglyceride, bilirubin and the like are directly quantitated, only a reaction product after a detection reaction is completed is measured. A measurement is carried out only at so called an end point, and thus detection is conducted only once at the minimum.

On the other hand, when the enzyme activity in the sample such as GOT, GPT, γGTP in the blood and the like is measured, it is acceptable to conduct detection only once, but a plurality of measurements (detection) are preferably carried out over time for enhancing accuracy (rate assay).

In this case, detection is only conducted at a plurality of points in the channel through which the final reaction solution is flown, namely at a plurality of positions with different distances (i.e. reaction time) from the point at which the solution is jointed with the reagent last mixed. For this purpose, it is necessary to provide a plurality of detection systems in the detection device and place the plurality of detection systems on the channel for the final reaction solution. Alternatively, if only one detection system is used, the detection (optical) device or the analyzing cartridge 1 needs to be shifted.

In the analyzing cartridge 1 of this embodiment, after the sample is separated and reacted with other reagents, the detection object is detected with a variety of methods in the downstream of the channel where the separation and reaction has been carried out.

For detection methods, a photo thermal converting detection method (e.g. Analysis No. 4 280-284 (1997)), an optical detection method such as a fluorometric method, an absorptiometric method and a chemiluminescence method, an electrochemical detection method using detecting electrodes, a method of measuring the number of blood cells by a change in electric resistance values, a method of measuring the number of blood cells by scattering, an immunological detection method by counting immunoassay and the like are used.

For the chemiluminescence method and fluorometric method, the detection object is changed into an excited compound in the presence of a catalyst such as an oxidant, and the energy, generated when the compound is changed from this state to the ground state (in the case of the fluorometric method, the energy generated when an energy acceptor is changed from the excited state to the ground state after the excited compound transfers energy to that coexisting energy acceptor), being released as light is detected. On the other hand, for the absorptiometric method, light is let in a solution containing the detection object to measure the transmitted light intensity, and the ratio of the transmitted light intensity to the incident light intensity is determined. In terms of sensitivity, it is generally said that the absorptiometric method, the fluorometric method and the chemiluminescence method are listed in the ascending sensitivity in the order.

For principal chemiluminescence reactions, methods by Luminol, Lucigenon and the like have been known since old times. The chemiluminescence reaction has advantages that detection can be carried out quickly and with high sensitivity, and detection devices are relatively inexpensive because no light sources are required for detection, etc. However, it has also disadvantages that luminescence is damped rapidly, the reagents are unstable, and backgrounds are high and so on. The fluorometric method also has an advantage that the reaction system has been known since old times, but an excitation light source, optical filters that separate excitation light and fluorescence and the like are required for the detection device.

These methods using luminous phenomena have disadvantages in detection of a very small amount of sample that light reception efficiency is not high because emitted light is diverged in all directions, and yields of emitting fluorescence are low in the case of the fluorometric method, and soon. For the absorptiometric method, the optical length should be increased for obtaining detection results of high accuracy, because the ratio between the incident light and transmitted light is detected in principle.

However, for a capillary having the wide and depth of about 1 to 1000 μm, the optical length in the front-to-back direction of the plate face of the analyzing cartridge 1 (not necessarily at right angles to the plane face of the analyzing cartridge 1), namely the optical length in a perpendicular or slanting direction relative to the flow of the liquid can not be much longer than the depth of the groove. If the concentration of the sample is sufficiently high, detection is possible even with the optical length almost as long as the depth of the groove (an optical path perpendicular to the plate face of the analyzing cartridge 1), but if the concentration is low, then it becomes difficult to carry out detection. Even if the concentration is low, detection can be carried out because an optical distance of about 1 to 10 mm can be obtained by providing an optical path in the direction in which the liquid is flown (the optical path in the plate face of the analyzing cartridge 1) but it has a disadvantage that the structure of the detection cell is complex.

For the electrochemical method, electrodes using substance-specific oxidation-reduction potentials such as glucose electrodes are used.

A thermal lens method (one of the photo thermal converting detection method) in which the sample in the liquid is excited with excitation light to form so called a thermal lens, and a change in the thermal lens is measured with detection light is also used as the detection method of the present invention (e.g. Japanese Patent Laid-Open No. 60-174933A, A. C. Boccara et. Al., Appl. Phys. Lett. 36, 130, 1980, J. Liquid Chromatography 12, 2575-2585 (1989), Japanese Patent Laid-Open No. 10-142177A (Molecule Biophotonics), Japanese Patent Laid-Open No. 4-369467A (Yokogawa Electric Corp.), Analysis No. 4, 280-284, 1997, M. Harada, et. al., Anal. Chem. Vol. 65, 2938-2940, 1993, Kawanishi, et. al., Japan Analytical Chemistry Society No. 44 Annual Conference Abstracts, p 119, 1995, etc.)

Now, the principle of the detection method using the thermal lens that is formed based on a photo thermal converting phenomenon will be described. Light with wavelengths that are absorbed by a measurement object dissolved in a solution (excitation light) is applied to a measured solution. Then, the measurement object is excited by the excitation light to generate heat (photo thermal converting effect). At this time, it is important that wavelengths of excitation light are selected so that this excitation light is not absorbed in contaminants other than the measurement object.

The generated heat is transmitted to a solvent near the portion irradiated with the excitation light to cause a local change in density, and by extension a change in refractivity. Because of this, the portion irradiated with the excitation light looks as if a concave lens were formed thereon in the presence of a substance absorbing excitation light.

Probe light with wavelengths different from those of the excitation light is applied to the portion that looks as if a concave lens were formed thereon. Because the probe light is refracted by the thermal lens, the amount of probe light captured by a light receiving element capturing probe light is decreased when the thermal lens is formed. The level of photo thermal converting effect is changed depending on the concentration of a measurement object, and therefore the measurement object can be quantified by measuring the level of the reduction of the above described light amount. Actually, for improving the S/N ratio, the excitation light is chopped, and a change in the amount of the probe light synchronized with its frequency is detected with a lock-in amplifier in general.

For a capillary having the wide and depth of about 1 to 1000 μm, the optical distance in the front-to-back direction of the plate face of the analyzing cartridge 1 (not necessarily at right angles to the plane face of the analyzing cartridge 1), namely the optical length in a perpendicular or slanting direction relative to the flow of the liquid can not be much longer than the depth of the groove, but if the photo thermal converting detection method is used, the measurement object can be detected in sufficiently high sensitivity even with this level of optical length.

If the photo thermal converting detection method is adopted, a complicated channel structure for providing a long optical distance is not required, thus making it possible to produce the analyzing cartridge 1 inexpensively, which is preferable. Also, detection can be conducted using a detection device with an inexpensive and simple optical system such as a combination of a semiconductor laser and a photodiode, which is preferable.

For the detection device using the photo thermal converting detection method, an excitation light source that has wavelengths absorbed by the detection object and is provided with outputs strong enough to form the thermal lens is required. For the excitation light source, light with required wavelengths may be taken out from a xenon lamp or the like by a prism, or a laser having wavelengths capable of exciting the detection object may be used.

For the laser, a He—Ne laser, an Ar laser, a carbon dioxide laser, a YAG laser or the like is used, but if a semiconductor laser is used, the detection device can be downsized, and thus the laser is suitable for uses such as POC analyses and the like. A condenser lens is needed so that the excitation light and probe light both come into a focus near the capillary channel.

A change in probe light is perceived by a photodiode, a CCD camera, and a photo multiplier tube. Furthermore, the photodiode is suitable for the downsizing of the detection device.

On the other hand, the excitation light is changed into pulse light of about 1 to 10 milliseconds by a chopper or the like, and only the change in probe light is detected by a lock-in amplifier or the like tuned with the chopper. The lock-in amplifier can be simplified with a single function semiconductor element or the like. Also, for the changing of excitation light into pulse light, the semiconductor laser may be modulated electrically.

In addition, when the probe light is detected, the lock-in amplifier is generally used, but means for shielding beams near the optical axes of pump light and probe light with a masking shield to detect only the probe light emitted by the thermal lens using the method of the dark field type photothermal converting spectroscopic analysis apparatus disclosed in Japanese Patent Laid-Open No. 9-229883 may also be adopted. Alternatively, the means may be replaced with an LSI with the function fixed for the pulse of excitation light.

The detection object is not limited as long as it absorbs excitation light, but the detection object should be separated from other substances in the sample, particularly substances absorbing excitation light, substances absorbing probe light or substances having fluorescence at the wavelengths of probe light before photothermal converting detection is carried out. For the level at which excitation light is absorbed, it is preferable in terms of sensitivity that the molar absorptivity is approximately in the range of from 1000 to 100,000.

The detection object absorbing no or little excitation light is converted into a substance absorbing excitation light (pigment for visible light) to be measured, with reactions using enzymes having the detection object as a substrate in combination. Alternatively, using an antibody against the detection object, the antibody or a secondary antibody is marked with a substance absorbing excitation light or an enzyme producing by reaction a substance absorbing excitation light to measure the substance absorbing excitation light directly produced or produced as a result of the enzyme reaction.

For example, in the case where a biological material is detected as a detection object, the material can finally be converted into the following substances by way of hydrogen peroxide, with enzyme reactions using the detection object as a substrate in combination (Aoyama, N. Clinical Examination, 41: 1014 (1997)).

That is, those substances are substances absorbing excitation light that are condensates of 4-aminoantipyrin with N-ethyl-N-(3-methylphenyl)-N'-acetylethylenediamine (EMAE), N-ethyl-N-(3-methylphenyl)-N'-succinylethylenediamine (EMSE), N-ethyl-N-(3-sulfopropyl)-3,5-dimethoxyaniline (DAPS), N-(3-sulfopropyl)-3,5-dimethoxyaniline (HDAPS), N-ethyl-N-(2-hydroxy-3-sulfopropyl)-3,5-dimethoxyaniline (DAOS), N-(2-hydroxy-3-sulfopropyl)-3,5-dimethoxyaniline (HDAOS), N-(2-hydroxy-3-sulfopropyl)-3,5-dimethoxyaniline (HSDA), N-ethyl-N-(2-hydroxy-3-sulfopropyl)-3-methylaniline (TOPS), N-ethyl-N-(2-hydroxy-3-sulfopropyl)-3-methylaniline (TOOS), N-ethyl-N-(2-hydroxy-3-sulfopropyl)-3,5-dimetylaniline (MAPS), N-ethyl-N-(2-hydroxy-3-sulfopropyl)-3,5-dimethylaniline (MAOS), N,N-bis(4-sulfobutyl)-3,5-dimethylaniline (MADB), N,N-bis(4-sulfobutyl)-3,5-dimethoxyaniline (DADB) and the like, or substances absorbing excitation light such as bis {4-[N-3'-sulfo-n-propyl-N-ethyl]amino-2,6-dimethylphenyl}methane (Bis-MAPS-C2), bis {4-[N-3'-sulfo-n-propyl-N-n-propyl]amino-2,6-dimethylphenil}methane (Bis-MAPS-C2), bis {4-[N-3'-sulfo-n-propyl-N-n-butyl]amino-2,6-dimethylphenyl}methane (Bis-MAPS-C4).

Figure 9:
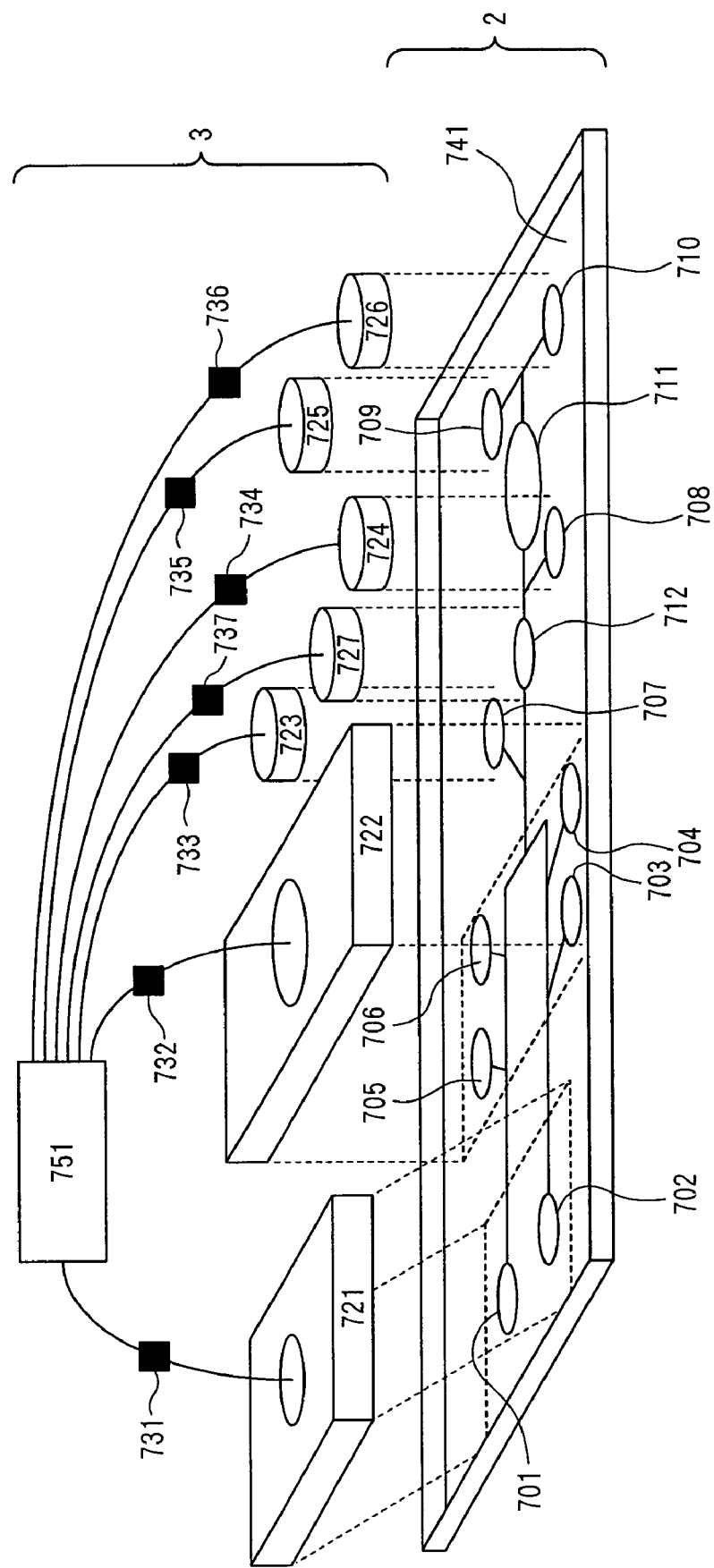
FIG. 9 is a conceptual view illustrating the configuration of the analyzing cartridge and a liquid feed control device.

An analyzing cartridge 2 and a liquid feed control device 3 of the second embodiment of the present invention will now be described using the conceptual view shown in FIG. 9. However, some parts are not shown for simplified explanation.

The analyzing cartridge 2 comprises the following items. That is, they are a plane member 741 having grooves on the lower face side, a cover sheet (not shown) bonded to the lower face of the plane member 741, a sample storing reservoir 710 for plasma, total blood and the like, a sample diluent storing reservoir 709, a sample measurement vessel 711, a sample dissolving liquid storing reservoir 707, a diluting and mixing vessel 712, a first reagent storing reservoir 704 for the measurement item 1 (e.g. total cholesterol), a second reagent storing reservoir 703 for the measurement item 1, a first reagent storing reservoir 706 for the measurement item 2 (e.g. glucose), a second reagent storing reservoir 705 for the measurement item 2, liquid waste storing reservoirs 701, 702 and 708, and capillaries connected for communication between reservoirs (shown by solid lines).

Also, the liquid feed control device 3 comprises the following items. That is, they are couplers 721 to 727 attached to the reservoirs, three-way valves 731 to 737, an air pressure pump 751, and tubes (shown by solid lines) connecting the above described respective members.

The reservoirs 701 to 709 and the diluting and mixing vessel 712 each comprise a through-hole of the plane member 741, a cover sheet (not shown) bonded to the lower face of the plane member 741, and a hydrophobic venting membrane (not shown) bonded to the upper face of the plane member 741, and are formed so as to have a predetermined volume. A predetermined amount of non-fluid reagent (not shown) is fixed in a dried form in each reagent storing reservoir 703 to 706.

The reagent dissolving liquid storing reservoir 707 is filled with a reagent dissolving liquid (a common buffer of the measurement items 1 and 2, an aqueous solution of a surfactant and the like). The reservoir is filled with solution by the system shown in FIG. 3 from a portion pack with the reagent dissolving liquid encapsulated therein, the mechanism thereof is neither described nor shown in FIG. 9.

Similarly, the sample diluent storing reservoir 709 is filled with a sample diluent (a buffer in which a surfactant may be added, or which may have an almost same composition as the reagent dissolving reagent) from the portion pack with the sample diluent encapsulated therein. The sample storing reservoir 710 is formed by a through-hole, into which plasma is introduced from the outside of the analyzing cartridge 2 (total blood may be added via a plasma separation membrane).

The sample measurement vessel 711 is not a though-hole (it may be a through-hole, but preferably, it is not a through-hole in terms of elimination of dead spaces), and is a groove that is identical in depth to the other channels but has a larger wide. And, the vessel is formed so that the area extending to the junction with the side channel connected to the liquid waste storing reservoir 708 has a predetermined volume, for example 0.7 μl. As described previously, the errors of this volume and the channel can be corrected by passing a standard solution through the measurement vessel and channel identical to the measurement vessel and channel through which the sample is passed.

The couplers 721 to 727 are attached to all the reservoirs 701 to 710 and the diluting and mixing vessel 712 from above the hydrophobic venting membrane. In FIG. 9, the liquid feed device 3 is shown in such a manner that the device is separated from the analyzing cartridge 2 for convenience in explanation, but at the time of analysis, the analyzing cartridge 2 and the couplers 721 to 727 of the liquid feed control device 3 are attached to each other via an appropriate packing or the like.

The couplers 721 to 727 are each connected to the air pressure pump 751 by tubes via the three-way valves 731 to 737 capable of being opened to the outside. Furthermore, the air pressure pump 751 may be a vacuum pump. Furthermore, when "close" is written in terms of these three-way valves 731 to 737 hereinafter, it means that the tube on the coupler side is closed.

The air pressure pump 751 and the three-way valves 731 to 737 are controlled by the computer of main body of the analysis apparatus in accordance with information recorded in a chip with a magnetic tape or the like.

The operations will be described below in chronological order.

The three-way valves 731 to 737 are closed. Then, the three-way valve 732 is opened to the outside, and the three-way valve 733 is opened so that pressure from the air pressure pump 751 is transferred to the coupler 723 for the reagent dissolving liquid storing reservoir 707 (hereinafter described as "the portion between the air pressure pump 751 and the couple 723 is opened"). Thus, the reagent dissolving liquid is fed into each reagent reservoir 703 to 706. Air in the midway channels and reagent reservoirs 703 to 706 is discharged to the outside through the vent, but the reagent dissolving liquid is blocked by the vent. In other words, a fixed volume of reagent dissolving liquid is fed into each reagent reservoir 703 to 706. The non-fluid reagent fixed in a freeze-dried form in each reagent reservoir 703 to 706 is immediately dissolved to become a homogenous reagent solution. Then, the three-way valves 732 and 733 are closed.

Then, when the three-way valve 736 is switched so that the portion between the air pressure pump 751 and the coupler 726 is opened, and the three-way valve 734 is opened to the outside, the sample in the sample storing reservoir 710 is flown into the liquid waste storing reservoir 708 through the sample measurement vessel 711. The feeding of the liquid is carried out for a time long enough to fill the sample measurement vessel 711 with plasma, and thereafter the three-way valves 734 and 736 are closed. Then, when the portion between the air pressure pump 751 and the coupler 725 is opened by the three-way valve 735, and the three-way valve 737 is opened to the outside, the sample diluent in the sample diluent storing reservoir 709 is flown into the diluting and mixing vessel 712 while carrying away and mixing with the plasma in the sample measurement vessel 711.

The air in the midway of the channel is discharged to the outside through the vent, and when the diluting and mixing vessel 712 is filled with the mixture (diluted sample), the inflow of the mixture is automatically stopped because it is blocked by the vent. The diluting and mixing vessel 712 has been prepared with the ratio in volume to the sample measurement vessel 711 set so that the sample can be diluted at a predetermined dilution ratio. In this way, the sample diluted at a predetermined dilution ratio is collected in the diluting and mixing vessel 712. Then, all the three-way valves 731 to 737 are closed on a temporary basis.

Thereafter, when the three-way valves 732 and 737 are opened so that pressure from the air pressure pump 751 is transferred to the couplers 722 and 727, and the three-way valve 731 is opened to the outside, the diluted sample and the respective reagent solutions are flown toward the liquid waste storing reservoirs 701 and 702. The flow rate at this time is set to be a predetermined value by pressure losses of the groove (depending on the sectional area and length of the groove and viscosity of each liquid), air pressure in each coupler and the like.

The mixing ratio of the diluted sample and each reagent solution is uniquely determined by this ratio of flow rates. In other words, the predetermined mixing ratio can be determined by the ratio of flow rates. The range extending from the junction of the first reagent solution and the diluted sample to the confluent with the second reagent solution corresponds to the reaction time for the first reagent solution, and the range extending from the confluent with the second reagent solution to the detection point (not shown) for analysis corresponds to the reaction time for the second reagent solution. This reaction time can be adjusted by setting predetermined values for the length of the channel and flow rate.

The detection method is not particularly limited as long as it is a method suitable for analysis of the liquid in a fine groove, such as a thermal lens detection method (photothermal converting detection method) and a fluorometric method. For the optical detection method, detection is preferably carried out in channels that are not covered with couplers. That is, in FIG. 9, detection is preferably carried out between the point at which the second reagent solution joins the mixture of the diluted sample and the first reagent solution and the liquid waste storing reservoir, and in the channels that are not covered with couplers 722 and 721.

Experimental Example 1

Measurement of Anti-Water Pressure of Hydrophobic Membrane

The anti-water pressure is measured at each average pore size for hydrophobic membranes of various kinds of materials. For the laboratory device for carrying out measurements, a device in which a disposable filter holder 810 with a membrane 800 set therein is attached to the tip of a syringe 820 with an inner diameter of 5 mm. The effective diameter of the membrane 800 is 3 mm. Furthermore, Figure (b) in FIG. 10 is a magnified sectional view of the filter holder 810 and the tip of the syringe 820.

For the measurement of anti-water pressure, the syringe 820 is first put in a test solution 830, and the syringe 820 is pushed against the a scale 840 while the syringe 820 is kept standing upright with its tip pointing upward, thereby carrying out a measurement. The air in the syringe 820 is pushed to the outside through the membrane 800, and a test solution 830 starts to seep through the membrane 800 if the syringe 820 is further pushed to gradually increase the pressure, and a value indicated by the scale 840 is read. Measurements were carried out ten times for each item, and the average value thereof was defined as an anti-water pressure value.

For the test solution 830, measurements were carried out for purified water (Japanese Pharmacopeia) and the reagent solution of the total cholesterol detection kit containing a surfactant (Trade name: Cholesterol E-HA Test Wako manufactured by Wako Pure Chemical Industry, Ltd.). Also, The membrane 800 is a PTFE membrane and a cellulose acetate membrane with the thickness of 150 μm, and the average size of the holes provided in the membrane 800 is 0.5 μm and 0.1 μm for both the PTFE membrane and cellulose acetate membrane. The results thereof are shown in Table 1.

The anti-water pressure of the reagent solution containing a surfactant was significantly low compared to water, irrespective of the material and average pore size of the membrane 800. Also, the smaller the average pore size, the higher was the anti-water pressure.

On the other hand, with respect to the material, PTFE showed a high anti-water pressure at each average pore size even in the case of the reagent solution, and had sufficient performance as a venting membrane. In contrast to this, cellulose acetate showed a low anti-water pressure (insufficient hydrophobicity), and thus was not preferable as a venting membrane for a reagent solution containing a surfactant.

TABLE 1

| Membrane Material | PTFE | | | | Cellulose Acetate | |
|---|---|---|---|---|---|---|
| Pore size[1] | 0.5 | | 0.1 | | 0.5 | 0.1 |
| Test Solution | Water | Reagent Solution | Water | Reagent Solution | Water | Reagent Solution |
| Anti-Water Pressure[2] | 3432 | 1731 | 5648 | 3662 | 37 | 12 |

[1] unit: μm
[2] unit: g/cm$^2$

Experimental 2

Reagent Dissolving Adjuvant

Commercially available reagent kits for use in diagnosis of blood components were used to examine dissolving time of reagents. A large number of holes with the diameter of 2 mm were bore in a PMMA plate with thickness of 2 mm, a PTFE porous membrane was bonded to the one face of the PMMA plate in a same way as Example 4 described later, and 2 μl of each reagent solution was put in the hole, followed by air-drying the same for 2 hours. The reagent kits that were used are as follows.

GOT, GPT: TA-LN Kainos (Kainos Co., Ltd.).
ALP: ALP Kainos (Kainos Co., Ltd.).
γGTP: EspaγGTP (N) (Nipro Co., Ltd.) and Aquaauto Kainos γGTP (Kainos Co., Ltd.).
t-Bil: HA Test Wako (Wako Pure Chemical Industries, Ltd.) and Espa TB (Nipro Co., Ltd.).
T. Chol: HA Test Wako (Wako Pure Chemical Industries, Ltd.).
TG: HA Test Wako (Wako Pure Chemical Industries, Ltd.) and Aquaauto Kainos TG (Kainos Co., Ltd.).
LDH: LDH Kainos (Kainos Co., Ltd.).
Gluc: Determiner GL-E (Kyowa Medix Co., Ltd.).
TP: Micro TP Test Wako (Wako Pure Chemical Industries, Ltd.) and Kainos Auto Series TP (Kainos Co., Ltd.).
ALB: ALB-A (International Reagents Corporation).
Cre: Determiner-L (Kyowa Medix Co., Ltd.) and L Type Wako (Wako Pure Chemical Industries, Ltd.).
HDL-Chol: Determiner L (Kyowa Medix Co., Ltd.)
LDL-Chol: Chole Test LDL (Daiichi Pure Chemicals Co., Ltd.).

Under microscopic examination, 2 μl of pure water was added in each of the above described holes, and was left standing still to observe states of dissolution. Almost all reagents were dissolved homogeneously in a few minutes, the No. 1 reagent solution of glucose (Determiner GL-E) and the like were not solved completely leaving a slight amount of insoluble matter, or non uniform concentrations were observed although they were dissolved.

Then, polyethylene glycol PEG 6000 was added in the No. 1 reagent solution of glucose (Determiner GL-E) so that the concentration was 1.8 mg/100 ml, and operations for injecting, air-drying and re-dissolving the same were carried out in a same way as described above. However, an insoluble matter was left again. Bovine albumin was added in the No. 1 reagent solution so that the concentration was 2.1 mg/100 ml, but a very similar result was obtained.

However, when glycerin was added in the No. 1 reagent solution so that the concentrations were 0.1%, 1% and 10%, and operations for injecting, air-drying and re-dissolving the same were carried out in a same way as described above, the No. 1 reagent solution was homogenously dissolved in a few minutes at any concentration.

Example 1

An example in which quantitative analysis of total cholesterol in blood serum was carried out using an analyzing cartridge with two reagents of the total cholesterol detection kid (Trade Name: Cholesterol E-HA Test Wako manufactured by Wako Pure Chemical Industries, Ltd.), a reagent dissolving liquid and a diluent encapsulated therein, and the standard serum (Determiner for Measurement of Standard Serum Lipid manufactured by Kyowa Medix Co., Ltd.) was used as a calibration solution to correct the result of analysis will be described. Furthermore, for the method of feeding the liquid, a method using electroosomosis flows by application of voltage was used.

Figure 12:
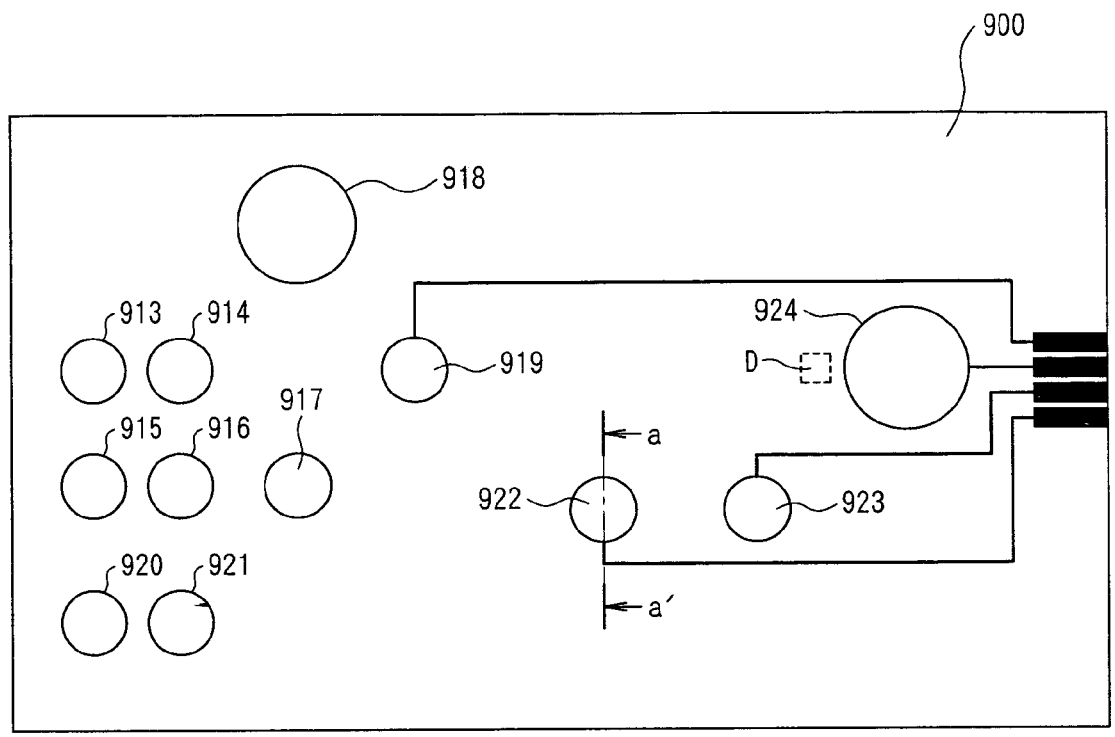
FIG. 12 shows the back face (plate face that does not have grooves) of the plane member of FIG. 11.
Figure 13:
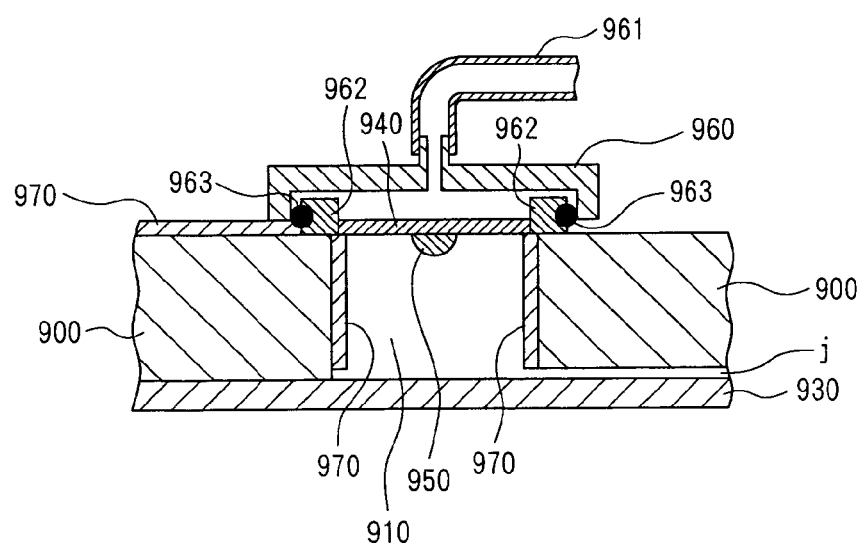
FIG. 13 is a sectional view of the a-a' line of the plane member of FIG. 12.

The analyzing cartridge 4 that was used and analysis operations will be described referring to the drawings. FIG. 11 shows a channel pattern of a plane member 900, and FIG. 12 shows the back face (face provided with no grooves) of the plane member 900 of FIG. 11. And, FIG. 13 is a sectional view of a portion of a reagent storing reservoir 910 of the plane member 900, taken along the a-a' line of FIG. 12, and is shown as an example for illustrating the structure of each reservoir. Thus, other reservoirs have almost same structures.

The analyzing cartridge 4 was produced by a cover sheet 930 made of PMMA with the thickness of 0.3 mm was bonded to the plane member 900 having grooves with an acryl-based double faced adhesive tape (MC 2030 manufactured by Nitto Denko Co., Ltd.). Furthermore, the plane member 900 is a plane member made of PMMA resin, formed through injection molding and having the thickness of 2 mm.

Grooves a to m are all 50 μm in both width and depth, and a measurement vessel A is 2 mm in diameter and 50μ in depth. In addition, reservoirs 901 to 912 each comprise a through-hole with a diameter of 2 mm.

Of respective openings 913 to 924 of the reservoirs 901 to 912, the openings 914, 916, 918, 919 and 921 to 924 are covered with a PTFE porous membrane 940, and the PTFE porous membrane constitutes a vent. A PTFE porous membrane with the pore size of 0.1 μm manufactured by Advantec Toyo Co., Ltd. (Product Number: T010A047A) was used for the PTFE porous membrane 940, and the porous membrane was bonded to the plane member 900 with a double-faced adhesive tape (Double-Faced Adhesive Tape for Bonding of Silicone Rubber No. 5302A manufactured by Nitto Denko Co., Ltd.).

Furthermore, a coupler 960 is attached to a coupler fixing frame 962 provided in the periphery of the above described vent. An O-ring 963 provided on the coupler fixing frame 962 exists between the coupler 960 and the coupler fixing frame 962, whereby the coupler 960 is kept constant with the frame airtightly. A three-way valve (not shown) is connected to each coupler 960 through a tube 961. Furthermore, each three-way valve is connected to a pressure pump (not shown) through a tube (not shown).

Also, as shown in FIGS. 12 and 13, a wiring 970 for application of voltage is formed by screen-printing of conductive paste because of the liquid feeding by electroosmotic flows. The wiring 970 is also printed on the inner wall of the reagent storing reservoir 910 by through-hole printing. The through-hole printing is a printing process that has recently been developed for providing electrical conductivity between the back face and the front face of the multilayer printed board, and this technique is required also for the plane member 900 of this embodiment.

A substance 950 obtained by drying reagents A and B of the total cholesterol detection kit into a solid is fixed in the PTFE porous membranes 940 of the reagent storing reservoirs 910 and 911. For the method for fixing the solid reagent 950 in the PTFE porous membrane 940, a method in which an appropriate amount of solution with the reagent dissolved in an appropriate amount of solvent is dropped onto the PTFE porous membrane 940 by a dispausing device (e.g. Pixsys 3000 manufactured by BioDot Co., Ltd.), and is dried was adopted. The reagent solution may be prepared with its concentration being consistent with the protocol appended to the total cholesterol detection kit, but more preferably, the concentration is increased by a factor of 2 to 3 to reduce the amount of liquid.

A pillow pack (not shown) in which about 100 µl of buffer for diluting the sample and calibration solution (e.g. 0.1 wt % of Triton X-100 solution, or phosphate buffer PBS containing 0.1 wt % of Triton X-100 solution) is encapsulated is inserted into the reservoir 901, and a pillow pack (not shown) with the standard serum encapsulated therein as a calibration solution is inserted into the reservoir 903.

Also, a pillow pack (not shown) in which about 100 µl of reagent dissolving liquid for dissolving the solid reagent 950 is encapsulated is inserted into the reservoir 908. At the time of analysis, the above described pillow packs are broken by a piston (not shown) installed in the analysis apparatus with the analyzing cartridge 4 mounted thereon to let the contained liquids flow into the reservoirs 902, 904 and 909.

A filter (not shown) for separating blood cells of the sample (GF-D manufactured by Whatman Co., Ltd. about 20 mm long and 5 mm wide) is attached to the reservoir 905. At the time of analysis, the collected sample is dropped into the reservoir 905, and the reservoir 905 is pressurized by the pressure pump, whereby the plasma after blood cells are filtered away is flown into the measurement vessel A.

The analysis procedure will be described below.

1) Sampling

50 µl of sample (blood) is collected from the subject, and is dropped into the reservoir 905.

2) Setting of Analyzing Cartridge 4

The analyzing cartridge 4 is mounted on an analysis apparatus having functions to perform a variety of operations for the detection device and analyzing cartridge 4.

3) With the three-way valve of the reservoir 909 being opened, and the three-way valves of the reservoirs 902, 904 to 907 and 910 to 912 being closed, the pillow pack containing the reagent dissolving liquid of the reservoir 908 is broken with the piston of the analysis apparatus to let the reagent dissolving liquid flow into the reservoir 909.

4) Preparation of Reagent Solution

With the three-way valves of the reservoirs 910 and 911 being opened, pressure is applied to the reservoir 909 to fill the reservoirs 910 and 911 with the reagent dissolving liquid to dissolve the solid reagent 950. At this time, the air in the reservoirs 910 and 911 is discharged through the PTFE porous membrane 940, but the reagent dissolving liquid is prevented from being leaked to the outside from the hydrophobic PTFE porous membrane 940. As a result, a certain amount of reagent dissolving liquid is introduced into the reservoir, and therefore a reagent solution in a certain concentration is prepared. Finally, for the purpose of turning on electricity, the three-way valve of the reservoir 912 is slightly opened, and the groove m is wetted with a liquid.

5) Measurement of Calibration Solution

With the three-way valves of the reservoirs 909 to 912 being closed, and the three-way valve of the reservoir 904 being opened, the pillow pack containing the calibration solution of the reservoir 903 is broken with the piston of the analysis apparatus to let the calibration solution flow into the reservoir 904. With the three-way valve of the reservoir 906 being opened, pressure is applied to the reservoir 904 to fill the measurement vessel A with the calibration solution to measure and collect 0.157 µl of solution. Excess calibration solution is stored in the liquid waste storing reservoir 906 (In the liquid waste storing reservoir 906, a water absorbing pad may be provided).

6) Dilution of Calibration Solution

With the three-way valves of the reservoirs 904 and 906 being closed, and the three-way valve of the reservoir 902 being opened, the pillow pack containing the diluent (buffer) of the reservoir 901 is broken with the piston of the analyzing apparatus to let the diluent flow into the reservoir 902. Then, with the three-way valve of the diluting vessel 907 being opened, pressure is applied to the reservoir 902 to let the diluent flow into the diluting vessel 907 with a volume of 6.28 µl together with the calibration solution of the measurement vessel A. At this time, the air in the diluting vessel 907 is discharged through the PTFE porous membrane 940, but the calibration solution and diluent are prevented from being leaked to the outside from the hydrophobic PTFE porous membrane 940.

In this way, 0.157 µl of calibration solution and 6.126 µl of diluent are introduced into the diluting vessel 907, and thereby diluted calibration solution diluted by a factor of 40 is prepared. Finally, for the purpose of turning on electricity, the three-way valve of the reservoir 909 is slightly opened, and the groove f is wetted with a liquid. When the feeding of the liquid is carried out by means of pneumatic pressure or gravity, this operation is not required.

7) Feeding of Diluted Calibration Solution and Reagent Solution, Reaction and Detection With the three-way valve of the reservoir 902 being closed, and the three-way valves of the reservoirs 907 and 910 to 912 being opened, voltage is applied to each reservoir, and the resulting electroosmotic flow is used to feed, mix and react each solution. Each applied voltage is adjusted so that a flow rate corresponding to a predetermined mixing ratio of the diluted calibration solution and two reagent solutions is obtained. The reaction product is quantitatively detected by the detection portion D of the thermal lens detection device installed in the analysis apparatus. The liquid waste after the reaction is completed is stored in the liquid waste storing reservoir 912, and is not discharged to the outside of the analyzing cartridge 4.

8) Cleaning of Measurement Vessel A and Diluting Vessel 907

With the three-way valves of the reservoirs 910 to 912 being closed, pressure is applied to the reservoir 902 to feed the diluent into the measurement vessel A. Thereby, the measurement vessel A is cleaned with the diluent, and the diluent after cleaning is stored in the diluting vessel 907. With the reservoir 902 being closed, and the reservoir 912 being opened, pressure is applied to the diluting vessel 907 to feed the diluent after cleaning into the reservoir 912. The above operations carried out three times to wash the measurement vessel A and the diluting vessel 907.

9) Filtration and Measurement of Sample

With the three-way valves of the reservoirs 902, 904, 907 and 909 to 912 being closed, and the three-way valve of the reservoir 906 being opened, pressure is applied to the reservoir 905 to fill the measurement vessel A with the sample while blood cells of the sample filtered away, and 0.157 μl of sample is measured and collected. The excess sample is stored in the liquid waste storing reservoir 906.

10) Dilution of Sample

With the three-way valves of the reservoirs 905 and 906 being closed, and the three-way valve of the diluting vessel 907 being opened, pressure is applied to the reservoir 902 to let the diluent flow into the diluting vessel 907 with a volume of 6.28 μl together with the sample in the measurement vessel A. At this time, the air in the diluting vessel 907 is discharged through the PTFE porous membrane 940, but the diluent is prevented from being leaked to the outside from the hydrophobic PTFE porous membrane 940. In this way, 0.157 μl of sample and 6.126 μl of diluent are introduced into the diluting vessel 907, and thereby a diluted sample diluted by a factor of 40 is prepared.

11) Feeding of Diluted Sample and Reagent Solution, Reaction and Detection

With the three-way valve of the reservoir 902 being closed, and the three-way valves of the reservoirs 907 and 910 to 912 being opened, voltage is applied to each reservoir, and the resulting electroosomotic flow is used to feed, mix and react each solution. Each applied voltage is adjusted so that a flow rate corresponding to a predetermined mixing ratio of the diluted sample and two reagent solutions is obtained (as in the case of the diluted calibration solution). The reaction product is quantitatively detected by the detection portion D of the thermal lens detection device installed in the analysis apparatus. The liquid waste after the reaction is completed is stored in the liquid waste storing reservoir 912, and is not discharged to the outside of the analyzing cartridge 4.

12) Calculation of Values Measured by Analysis

A calibration curve is prepared based on values measured by analysis of the calibration solution of which total cholesterol value is known, and thereby the total cholesterol value is determined from the value measured by analysis of the sample. For detection methods, the method described in International Publication WO/64846 by the inventor and the like can be adopted. As a result of this Example, the concentration of total cholesterol was 98 mg/dl. On the other hand, as a result of analyzing the sample directly by a "hand method" that is generally used at clinical laboratories and the like, the concentration was 104 mg/dl.

Example 2

Another example in which the quantitative analysis of total cholesterol in the blood serum was carried out using an analyzing cartridge as in the case of Example 1 will be described. However, in this example, a method using air pressure was used as the method of feeding the liquid.

For the analyzing cartridge 5, a cartridge same as that of FIGS. 11, 12 and 13 (Example 1) was used except that no electrodes and wirings are provided, and therefore this example will be described using FIGS. 11, 12 and 13 as well. In addition, various kinds of operations and procedures are also almost identical to those of Example 1, and therefore the analysis procedures will be described below only for differences relative to Example 1.

1) to 3)

The procedures are identical to those of Example 1.

4) Preparation of Reagent Solution

The procedures are same as those of Example 1, but the operation of wetting the groove m with a liquid is not carried out.

5) Filtration and Measurement of Sample

The procedures are identical to those of Example 1.

6) Dilution of Sample

The procedures are same as those of Example 1, but the operation of wetting the groove f with a liquid is not carried out.

7) Feeding of Liquid, Reaction and Detection

With the three-way valve of the reservoir 902 being closed, and the three-way valve of the reservoir 912 being opened, predetermined air pressure is applied to the three-way valves of the reservoirs 907, 910 and 911 to feed, mix at a predetermined ratio and react the liquid. Each mixing ratio is adjusted by applied pressure. The reaction product is quantitatively detected by the detection portion D of the thermal lens detection device installed in the analysis apparatus. The liquid waste after the reaction is completed is stored in the liquid waste storing reservoir 912, and is not discharged to the outside of the analyzing cartridge 5. Furthermore, a water absorbing pad may be provided in the liquid waste storing reservoir 912.

Example 3

The method of producing the analyzing cartridge 4 as described above and the method of dissolving reagents in the analyzing cartridge 4 will be described in detail.

1) Description of Plane Member 900

Injection molding using PMMA resin was carried out to obtain the plane member 900 constituting the analyzing cartridge 4. This plane member 900 is 2 mm in thickness, and has a groove pattern as shown in FIG. 11. The grooves a to m are all 50 μm in both width and depth. And, it comprises a recess well having a diameter of 2 mm and depth of 50 μm, and the recess well constitutes the measurement vessel A. Also, it has through-holes each having a diameter of 2 mm, and the through-holes constitute reservoirs 901 to 912.

2) Press of Venting Membrane

Using a cyclic mold having an outer diameter of 4 mm and inner diameter of 3 mm (width of 1 mm), the PTFE porous membrane 940 was pressed to deprive the pressed portions of porosity. The press was conducted in accordance with the locations of the through-holes (reservoirs 901 to 912) in the plane member 900 so that the portions deprived of porosity by being pressed surround each through hole. For the press conditions, the temperature is 20° C. and pressure is 176 MPa.

The pressed portion is a non-gas permeable portion, and therefore in the PTFE porous membrane 940, the gas is not passed in the lateral direction.

Furthermore, for the PTFE porous membrane 940, a PTFE with the pore size of 0.1 μm manufactured by Advantec Toyo Co., Ltd. (Product Number: T010A047A) was used.

3) Bonding of Venting Membrane

The PTFE porous membrane 940 pressed as described above was bonded to the plane member 900 using a double-faced adhesive tape. For this double-faced adhesive tape, Double-faced Adhesive Tape for Bonding Silicone Rubber No. 5302 A manufactured by Nitto Denko Co., Ltd. was used. However, a circular hole having the diameter of 2 mm is provided in the position in the double-faced adhesive tape corresponding to each through-hole of the plane member 900.

4) Dispensation of Reagent Solution

The reagent solution was dispensed into the reservoirs 910 and 911 of the plane member 900 with the venting membrane bonded thereto. Using Pixsys 3000 manufactured by BioDot Co., Ltd. for the dispensing device, the reagent solution was doted onto the PTFE porous membrane 940 from the plane member 900 side. Furthermore, the concentration of the reagent solution and the amount of injection are set so that the concentration of the reagent in a reagent dissolving liquid can be a predetermined concentration when each reservoir is filled with the reagent dissolving liquid.

5) Drying of Reagent Solution

The plane member 900 with the reagent solution dispensed therein was left standing still for about an hour at 20° C. and 30% RH, thereby vaporizing water to dry the solution to fix the reagent on the PTFE porous membrane 940. If the solution is dried under a reduced pressure, it can be dried in about ten minutes, but some caution is required to prevent the bumping of the reagent solution.

6) Mounting of Portion Pack

A portion pack having encapsulated therein about 100 μl of reagent dissolving liquid for dissolving each reagent was prepared, and was mounted in the position of the reservoir 908 of the plane member 900. For the reagent dissolving liquid, a solution obtained by dissolving Triton X100 in distilled water in a concentration of 1 wt % was used.

7) Bonding of Cover Sheet 930

The cover sheet 930 made of PMMA with a thickness of 300 μm was bonded to the plane member 900 processed as described above to complete the analyzing cartridge 4. The cover sheet 930 and the plane member 900 were bonded together using an acryl based double faced adhesive tape (MC 2030 manufactured by Nitto Denko Co., Ltd.).

Furthermore, the process of producing analyzing cartridge capable of analysis for a plurality of analysis items is same as the process described previously (See FIG. 7). Even a large number of reagents can be injected at a time with the above described dispensing device (Pixsys 3000), and the production is effective.

8) Feeding of Diluent and Dissolution of Reagent

The analyzing cartridge 4 was mounted on the analysis apparatus having a piston to push the portion pack, and a coupler for applying pressure to the vent was attached to the reservoir 909. The portion pack of the reservoir 908 was pushed with the above described piston to let the reagent dissolving liquid flow into the reagent dissolving liquid dropping reservoir 909. Subsequently, the vent of the reservoir 909 was pressurized with the coupler to feed the reagent dissolving liquid into reservoirs 910 and 911. Then, the air in the reservoirs 910 and 911 was purged, and the reservoirs 910 and 911 were filled with the reagent dissolving liquid to dissolve the reagent in the reservoirs 910 and 911, whereby reagent solutions in a predetermined concentration was prepared.

Example 4

Figure 14:
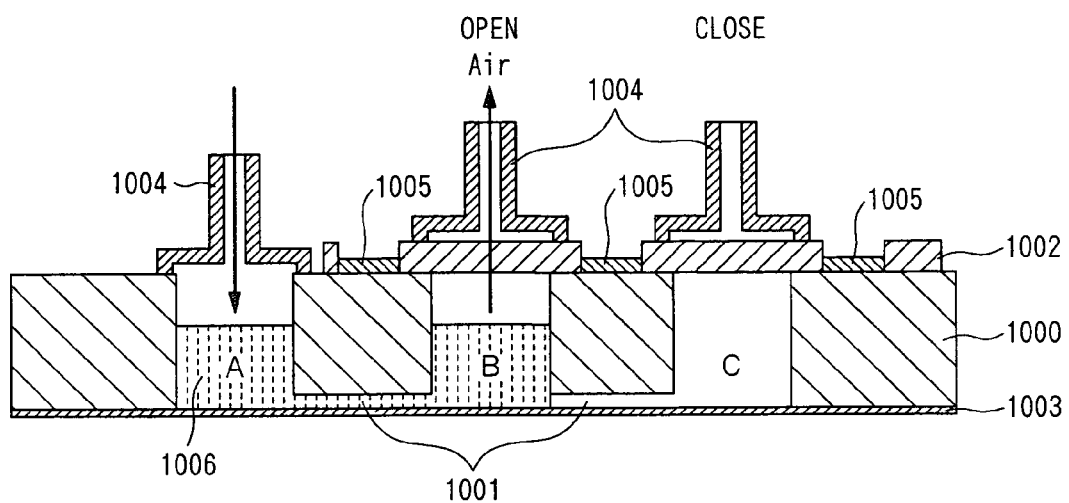
FIG. 14 is a sectional view illustrating the structure of the analyzing cartridge having vents in a state in which a gas is not permeated in the lateral direction, and the behavior of the gas.
Figure 15:
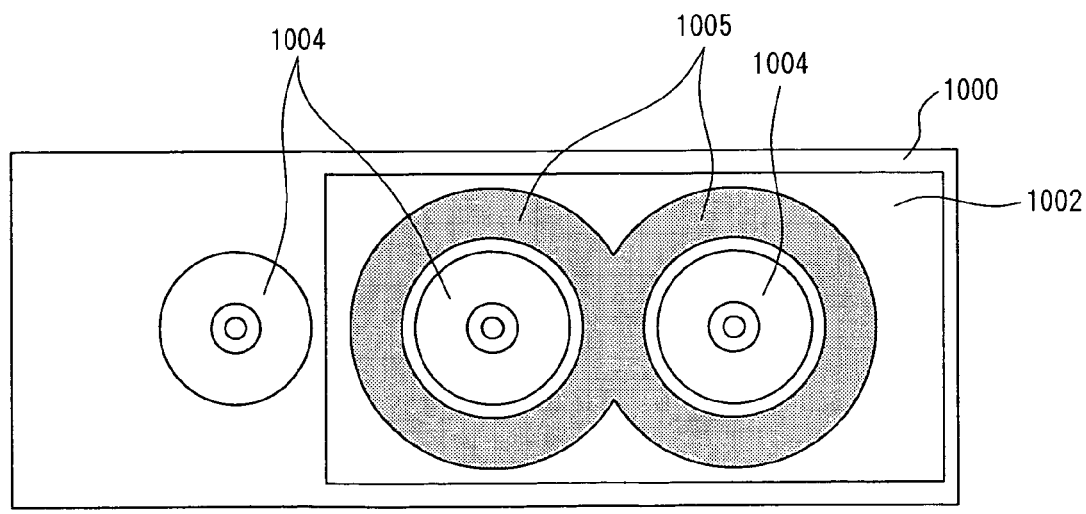
FIG. 15 is a plan view of the analyzing cartridge of FIG. 14.

An example in which pressure was applied to the portion of the venting membrane surrounding the opening of the reservoir, whereby the air was prevented from being passed in the lateral direction in the venting membrane to control with high accuracy the feeding of the liquid in the analyzing cartridge will be described in detail referring to FIGS. 14 and 15.

A plane member 1000 made of PMMA with the thickness of 2 mm was formed by injection molding. This plane member 1000 is provided with three through-holes each having a diameter of 2 mm, and the through-holes communicate with one another through a groove 1001 with the width of 100 μm and the depth of 50 μm.

A cover sheet 1003 made of PMMA with the thickness of 0.3 mm was bonded to the face of this plane member 1000 having the groove 1001. Also, a venting membrane 1002 was bonded to the other face using a double-faced adhesive tape (No. 5302 A manufactured by Nitto Denko Co., Ltd.). Then, a valued coupler 1004 was attached to the above described other face of the plane member 1000 in such a manner as to cover the openings of reservoirs A, B and C constituted by the above described through-holes to prepare the analyzing cartridge.

For the venting membrane 1002, a PTFE porous membrane with the pore size 0.1 μm (Product Number: T010A047A manufactured by Advantec Toyo Co., Ltd.) was used. And, a cyclic portion 1005 of the venting membrane 1002 surrounding the openings of the reservoirs B and C has been pressed under a pressure of 176 MPa at 20° C., and thus the cyclic portion 1005 is deprived of porosity (See FIG. 15).

With the valve of the reservoir B being opened, and the valve of the reservoir C being closed, pressure was applied to 1% aqueous solution 1006 of Triton X100 (Wako Pure Chemical Industries, Ltd.) in the reservoir A, thereby feeding the aqueous solution 1006 from the reservoir A to the reservoir B. Because the cyclic portion 1005 of the venting membrane 1002 surrounding the openings of the reservoirs B and C is deprived of porosity, air could not be passed in the lateral direction in the venting membrane 1002. Thus, air could not be leaked from the opening of the reservoir C through the membrane 1002 to the coupler 1004 of the reservoir B. As a result, the reservoir B could be filled with the aqueous solution 1006 with no aqueous solution 1006 being fed into the reservoir C (See FIG. 14). Furthermore, in FIG. 14, the air behaviors (flows) are shown by arrows.

Comparative Example

An analyzing cartridge was prepared in a same way as the above described Example 4. However, the venting membrane 1002 has not been pressed, and thus air could be passed in the lateral direction in the venting membrane 1002.

Figure 16:
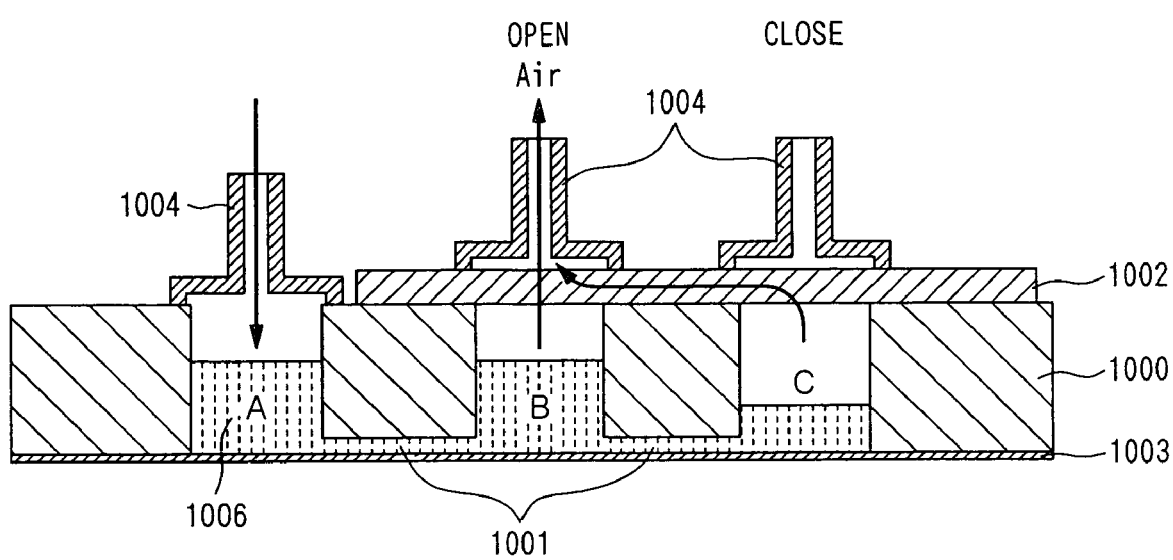
FIG. 16 is a sectional view illustrating the structure of the analyzing cartridge having vents in a state in which a gas is permeated in the lateral direction, and the behavior of the gas.

With the valve of the reservoir B being opened, and the valve of the reservoir C being closed, pressure was applied to 1% aqueous solution 1006 of Triton X100 (Wako Pure Chemical Industries, Ltd.) in the reservoir A, thereby feeding the aqueous solution 1006 from the reservoir A to the reservoir B. However, because air could be passed in the lateral direction in the venting membrane 1002, air was leaked from the reservoir C through the venting membrane 1002 to the coupler 1004 of the reservoir B as shown by the arrow. As a result, despite the fact that the valve of the reservoir C was closed, the aqueous solution 1006 was also fed into the reservoir C (See FIG. 16).

INDUSTRIAL APPLICABILITY

As described above, if the analyzing cartridge of the present invention is used, POC analysis and the like can be carried out with very small amounts of sample and reagent, conveniently, for a short time and inexpensively. Also, management of reagents and maintenance carried out by the analysis operator at the time of analysis can be relieved. In addition, there are little limitations for the detection reaction, and analysis for a large number of items can be performed at a time.

Also, according to the liquid feed control device, the feeding of liquids such as a sample and reagent solutions in the above described analyzing cartridge can be controlled with high accuracy, and the liquid feed control device can be produced inexpensively.

The invention claimed is:

1. A method of analyzing a sample comprising the steps of:
    feeding a reagent dissolving liquid from a reagent dissolving liquid storing reservoir in an analyzing cartridge in which said reagent dissolving liquid for dissolving a reagent is stored to a reagent storing reservoir in said analyzing cartridge in which a reagent for use in the analysis is stored through capillaries connected for communication between these reservoirs, at least one of said reservoirs having an opening leading to the outside of the analyzing cartridge, at least one of the reservoirs having an opening being covered with a gas-permeable/non-liquid-permeable vent, the reagent being located in at least one of said reservoirs having an opening covered with a vent;
    dissolving a non-fluid reagent located in said reagent storing reservoir, in said reagent dissolving liquid in said reagent storing reservoir when a portion pack containing the reagent dissolving liquid and made of aluminum coated polyethylene, polyethylene, polypropylene, polyvinyl chloride, polycarbonate or polymethylpentene sheet material is broken to introduce the reagent dissolving liquid into the reagent dissolving liquid storing reservoir which liquid is then fed to the reagent storing reservoir to prepare a reagent solution in the analyzing cartridge immediately before analysis is carried out;
    introducing a sample into said reagent solution in said reagent storing reservoir; and
    carrying out an analysis of said sample in said reagent solution in said reagent storing reservoir;
    wherein the portion pack is broken with a pin for breaking the portion pack that is provided with the portion pack or is broken with pressure caused by pressing over the vent to discharge reagent dissolving liquid contained in the portion pack when the portion pack is located in the analyzing cartridge with a part thereof covered by the vent.

2. The method of analyzing a sample according to claim 1, including mixing and reacting together a sample which is liquid and said reagent solution in said reagent storing reservoir using said capillaries.

3. The method of analyzing a sample according to claim 1, wherein said vent is composed of a hydrophobic member having pores.

4. The method of analyzing a sample according to claim 3, wherein said hydrophobic member having pores is a hydrophobic porous membrane.

5. The method of analyzing a sample according to claim 4, wherein the openings of a plurality of reservoirs are covered with a common hydrophobic porous membrane to form respective vents, and the portions of said hydrophobic porous membrane located between the reservoirs are deprived of porosity.

6. The method of analyzing a sample according to claim 5, wherein the portions of said hydrophobic porous membrane located between the reservoirs are deprived of porosity by applying pressure to the portions.

7. The method of analyzing a sample according to claim 1, wherein said analyzing cartridge includes, in addition to said reservoir containing said reagent, a calibration solution storing reservoir for storing a calibration solution for calibrating the result of analysis, a sample storing reservoir for storing a liquid sample, a diluent storing reservoir for storing a diluent for diluting said calibration solution and said sample, a measuring reservoir for measuring said calibration solution and said sample, and a diluting reservoir for mixing said measured calibration solution or said measured sample with said diluent to dilute the same, and a capillary is connected for communicating said measuring reservoir with said calibration solution storing reservoir, with said sample storing reservoir, with said diluent storing reservoir and with said diluting reservoir, respectively.

8. A method of analyzing a sample according to claim 7, that includes:
    a calibration solution measuring step of measuring said calibration solution by feeding said calibration solution from said calibration solution storing reservoir into said measuring reservoir;
    a calibration solution diluting step of feeding said diluent from said diluent storing reservoir into said measuring reservoir, thereby feeding said diluent and said calibration solution in said measuring reservoir into said diluting reservoir to mix said calibration solution and said diluent together to dilute said calibration solution;
    a calibration solution analyzing step of reacting said diluted calibration solution with said reagent to obtain the value measured by analysis of said diluted calibration solution;
    a sample measuring step of measuring said sample by feeding said sample from said sample storing reservoir into said measuring reservoir;
    a sample diluting step of feeding said diluent from said diluent storing reservoir into said measuring reservoir, thereby feeding said diluent and said sample in said measuring reservoir into said diluting reservoir to mix said sample and said diluent together to dilute said sample;
    a sample analyzing step of reacting said diluted sample with said reagent to obtain the value measured by analysis of said diluted sample; and
    a calibrating step of calibrating the value measured by analysis of said sample using the value measured by analysis of said calibration solution.

9. The method of analyzing a sample according to claim 1, wherein said analyzing cartridge includes, in addition to said reservoir containing said reagent, a sample storing reservoir for storing a liquid sample, a diluent storing reservoir for storing a diluent for diluting said sample, a measuring reservoir for measuring said sample, and a diluting reservoir for mixing said diluent with said measured sample to dilute the same, and a capillary is connected for communicating said measuring reservoir with said sample storing reservoir, with said diluent storing reservoir and with said diluting reservoir, respectively.

10. A method of analyzing a sample according to claim 9, that includes:
- a sample measuring step of measuring said sample by feeding said sample from said sample storing reservoir into said measuring reservoir; and
- a sample diluting step of feeding said diluent from said diluent storing reservoir into said measuring reservoir, thereby feeding said diluent and said sample in said measuring reservoir into said diluting reservoir to mix said sample and said diluent together to dilute said sample.

11. The method of analyzing a sample according to claim 1, including a liquid feed control device attached to the analyzing cartridge that controls the feeding of a liquid between said any reservoirs via said capillaries by allowing or regulating the entry/exit of a gas via said vent, thereby letting said liquid flow into said reservoirs or letting said liquid flow from said reservoirs via said capillaries.

12. The method of analyzing a sample according to claim 11, wherein the liquid feed control device includes valves placed in positions opposite to said reservoirs with said vents therebetween, in which the entry/exit of the gas via said vents is allowed or regulated by the valves.

13. The method of analyzing a sample according to claim 11, wherein the liquid feed control device includes couplers placed in positions opposite to said reservoirs with said vents therebetween, and attached to said vents in such a manner as to cover said openings, pumps coupled to said couplers, and valves placed between said couplers and said pumps, in which the entry/exit of the gas via said vents is allowed or regulated by at least one of said pump or said valve.

* * * * *